US006586596B2

(12) United States Patent
Chalmers et al.

(10) Patent No.: US 6,586,596 B2
(45) Date of Patent: Jul. 1, 2003

(54) ACETYLCHOLINE ENHANCERS

(75) Inventors: Derek T. Chalmers, Solana Beach, CA (US); Susumo Sato, Chiba (JP); Tadayuki Koda, Chiba (JP)

(73) Assignee: SSP Co., Ltd., Tokyo (JP)

( * ) Notice: Subject to any disclaimer, the term of this patent is extended or adjusted under 35 U.S.C. 154(b) by 0 days.

(21) Appl. No.: 09/836,069

(22) Filed: Apr. 17, 2001

(65) Prior Publication Data

US 2001/0039284 A1 Nov. 8, 2001

Related U.S. Application Data

(62) Division of application No. 09/328,643, filed on Jun. 9, 1999.
(60) Provisional application No. 60/088,737, filed on Jun. 10, 1998, provisional application No. 60/091,666, filed on Jul. 2, 1998, provisional application No. 60/109,413, filed on Nov. 20, 1998, provisional application No. 60/115,089, filed on Jan. 7, 1999, and provisional application No. 60/136,887, filed on Jun. 1, 1999.

(51) Int. Cl.[7] .............................................. C07D 401/06
(52) U.S. Cl. ........................................................ 546/84
(58) Field of Search .............................................. 546/84

(56) References Cited

U.S. PATENT DOCUMENTS

| 5,190,951 A | 3/1993 | Hasegawa et al. | .......... 514/292 |
| 5,240,934 A | 8/1993 | Hasegawa et al. | .......... 514/326 |
| 5,300,517 A | 4/1994 | Hasegawa et al. | .......... 514/290 |

FOREIGN PATENT DOCUMENTS

| CA | 2135253 | 8/1996 |
| EP | 0 481 429 A2 | 4/1992 |

*Primary Examiner*—Fiona T. Powers
(74) *Attorney, Agent, or Firm*—Michael P. Straher; Cozen O'Connor

(57) ABSTRACT

Disclosed herein are quinoline derivatives having dual mechanistic properties, referred to in this patent document as "acetylcholine enhancers", i.e., compounds which evidence acetylcholinesterase (AChE) inhibition activity, and 5-HT3 receptor antagonist activity. A particularly preferred compound is 2-[2-(1-benzylpiperizin-4-yl)ethyl]-2,3-dihydro-9-methoxy-1H-pyrrolo [3,4-b] quinolin-1-one hemifumarate, referred to herein as Compound A ("Cm.A").

1 Claim, 20 Drawing Sheets

ACETYLCHOLINE ENHANCERS

This Application is a divisional of application Ser. No. 09/328,643 filed Jun. 9, 1999.

CROSS REFERENCE TO RELATED APPLICATIONS

This application claims benefit of U.S. Provisional Application Ser. No. 60/088,737, filed via U.S. Express Mail on Jun. 10, 1998; U.S. Provisional Application Ser. No. 60/091,666, filed via U.S. Express Mail on Jul. 2, 1998; U.S. Provisional Application Ser. No. 60/109,413, filed via U.S. Express Mail on Nov. 20, 1998; and U.S. Provisional Application Ser. No. 60/115,089, filed via Express Mail on Jan. 7, 1999, and U.S. Provisional Application Ser. No. 60/136,887 entitled "Acetylcholine Enhancers" filed Jun. 1, 1999 in the names of Derek T. Chalmers, Susumu Sato and Tadayuki Koda. The contents of the foregoing applications are incorporated herein by reference in their entireties.

FIELD OF THE INVENTION

The present invention generally relates to quinoline derivatives, more particularly to quinoline derivatives which are acetylcholine enhancers, and specifically to the acetylcholine enhancer N-[2-(1-Benzylpiperizin-4-yl)ethyl]-2,3-dihydro-9-methoxy-1H-pyrrolo[3,4b] quinolin-1-one hemifurnarate, referred to herein as Compound A ("Cm.A").

BACKGROUND OF THE INVENTION

Alzheimer's disease ("AD") is a disorder of unknown etiology. A pervasive and deleterious effect of AD is a decreasing deficit in cognitive function. Several approaches to the treatment of this disorder are currently being investigated. To date, however, only one therapeutic approach has evidenced sufficient clinical safety and efficacy to warrant approval for commercialization by the United States Food and Drug Administration ("FDA"). This therapeutic approach focuses on inhibition of acetylcholinesterase ("AChE"). AChE is an enzyme that degrades the neurotransmitter acetylcholine ("ACh"). By inhibiting this degradation process, the ACh neurotransmitter remains in the neural cleft for increased time periods, thereby increasing the chemical and functional effects of the neurotransmitter, e.g., improvement in cognitive function. Two such AChE inhibitors approved by the FDA are 1,2,3,4-tetrahydro-9-acridinamine (tacrine, THA; "COGNEX") and donepezil (E2020; "ARICEPT"). An AChE inhibitor approved for commercialization in Europe is rivastigmine (ENA713; "EXELON"). A significant side effect associated with all three of these compounds is nausea and/or vomiting. This side effect can limit the maximum dose that a physician may otherwise desire to provide to a patient, for obvious reasons, e.g., the side effect may cause patients to not take all of the required doses, or the side effect may cause patients to stop taking the medication entirely.

While inhibition of AChE is one approach to resolving clinical deficits associated with AD, another approach would be to increase production of ACh. It has been reported that antagonists to the serotonin receptor 5-HT3, increase the neuronal release of ACh. See for example Ramirez, M J., et al., 712:2 *Brain Res.* 274 (1996); Crespi, D., et al. 35:4 *Pharmacol. Res.* 351 (1997); and Roychoudhurg, M. and Kulkani, S. K., 19:1 *Methods Find Exp. Clin. Pharmacol.* 43 (1997). It has also been reported that the density of 5-HT3 receptor recognition sites are not altered in patients with AD as compared to age-matched controls. Barnes, N. M., et al., 1:3–4 *Neuroreport.* 253 (1990). Antagonists to the 5-HT3 receptor are also reported to inhibit emesis (i.e., vomiting). See, e.g., Parikh, P. M. et al. 33:1 *Indian J. Cancer* 17 (1996).

Quinoline derivatives having AChE activity have been disclosed. U.S. Pat. Nos. 5,190,951; 5,540,934; and 5,300,517.

Compounds having multiple therapeutic mechanisms are desirable. For example, a compound that can both inhibit AChE activity and increase the neuronal production of ACh would be preferred for the treatment of neurological disorders such as AD, where the beneficial link between ACh, inhibition of AChE, and AD have been clinically established. This invention is directed to this, as well as other, important ends.

SUMMARY OF THE INVENTION

The present invention provides selected quinoline derivatives which are ACh enhancers. In some preferred embodiments, acetylcholine enhancers are provided that have the structure:

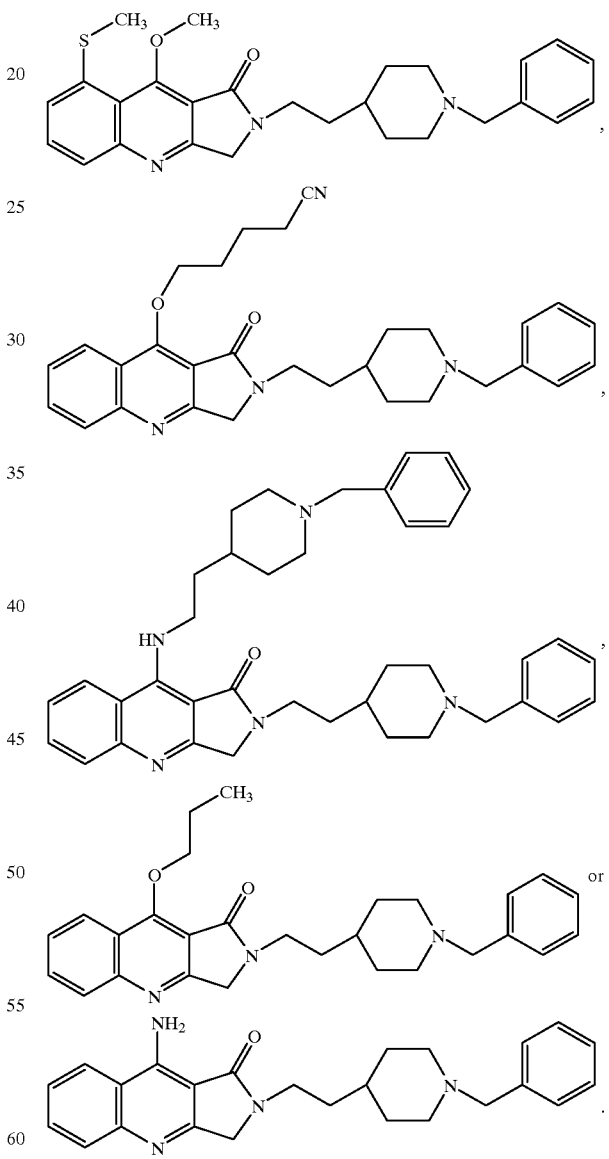

In some preferred embodiments, the acetylcholine enhancers are pharmaceutically acceptable salts of the foregoing compounds. A particularly preferred ACh enhancer is N-[2(1-Benzylpiperizin-4-yl)ethyl]2,3-dihydro-9-methoxyl-1H-pyrrolo[3,4-b]quinolin-1-one, i.e.,

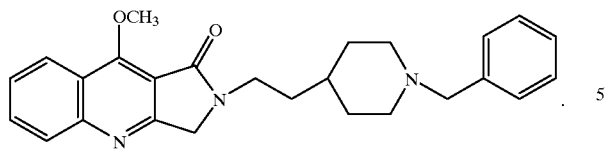

In one particularly preferred embodiment, the acetylcholine enhancer is N-[2-(1-benzylpiperizin-4-yl)ethyl]-2,3-dihydro-9-methoxy-1H-pyrrolo[3,4b]quinolin-1-one heimfumatate, i.e.:

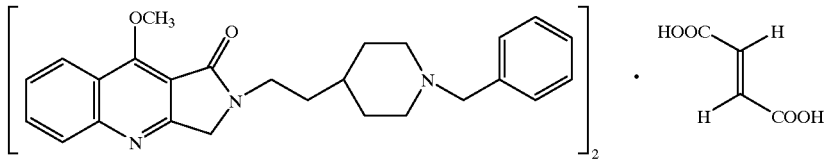

referred to herein as Compound A ("Cm.A.").

Also provided in accordance with the invention are methods for both inhibiting the enzyme acetylcholine esterase, and antagonizing the serotonin 5HT3 receptor in a system that comprises both acetylcholine esterase and the serotonin 5HT3 receptor. In preferred embodiments, the methods comprise introducing to the system an acetylcholine enhancer, preferably selected from the group consisting of compounds of formula:

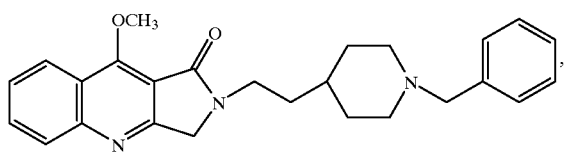

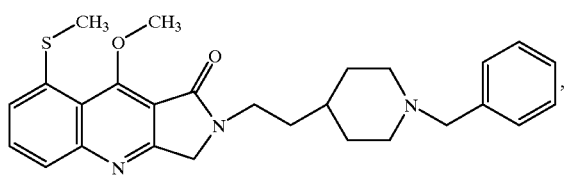

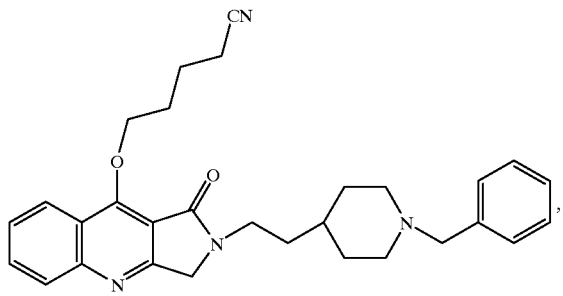

-continued

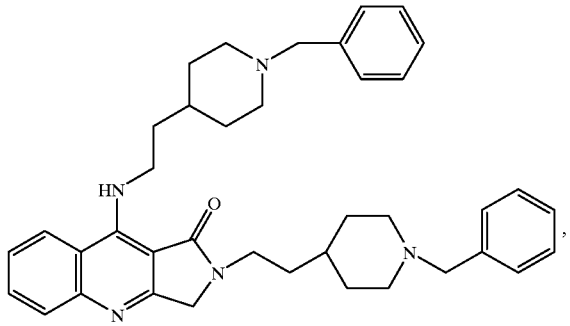

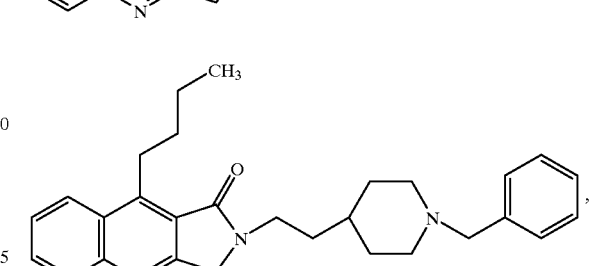

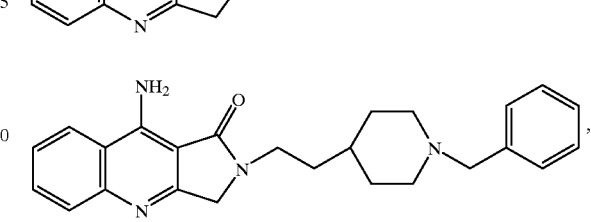

and pharmaceutically acceptable salts thereof.

In some more preferred embodiments, the compound is

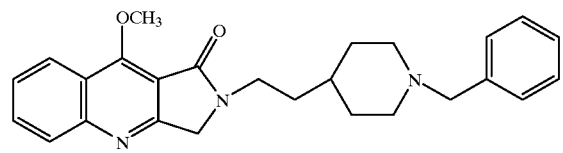

or a pharmaceutically acceptable salt thereof. In even more preferred embodiments, the acetylcholine enhancer has the formula:

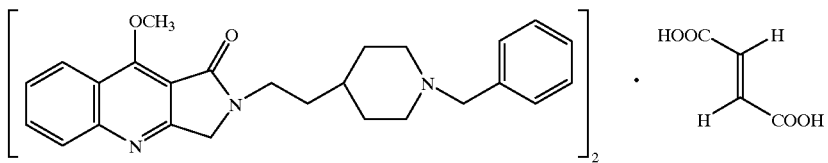 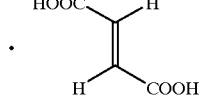

The present invention also provides pharmaceutical compositions comprising acetylcholine enhancers. In preferred embodiments, the pharmaceutical compositions comprise a compound of formula:

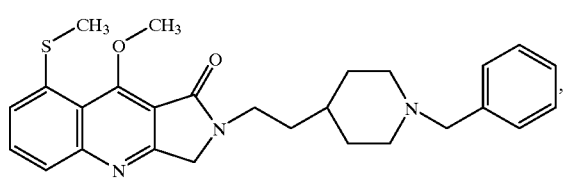

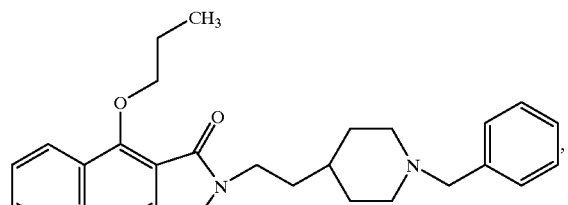

-continued

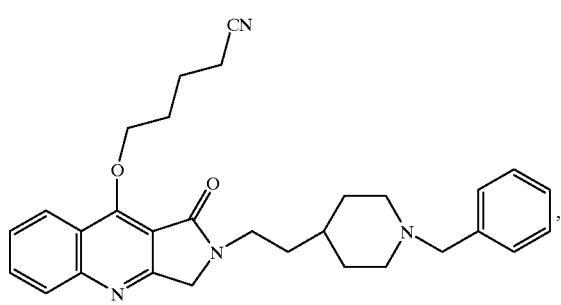

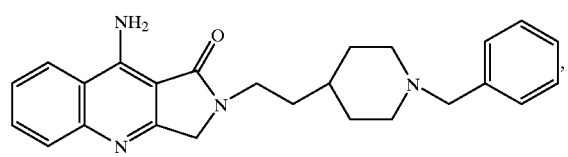

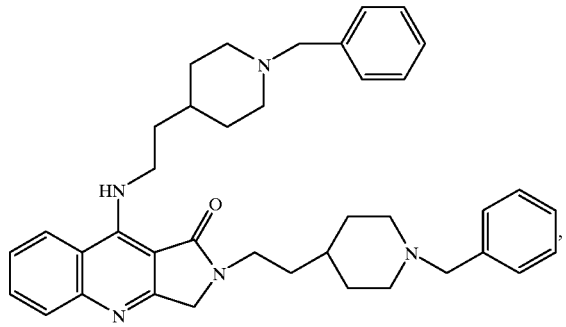

or pharmaceutically acceptable salts thereof.

In further preferred embodiments, the pharmaceutical composition comprises a compound of formula:

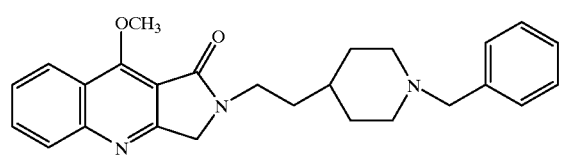

or a pharmaceutically acceptable salt thereof, which is preferably

 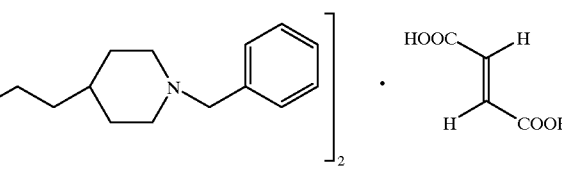 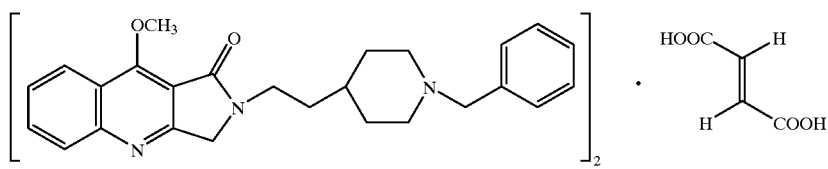 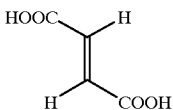

The present invention also provides methods of both inhibiting the enzyme acetylcholine esterase and antagonizing the serotonin 5HT3 receptor comprising providing an individual in need of inhibiting acetylcholine esterase and antagonizing the serotonin 5HT3 receptor with a pharmaceutical composition of the invention, which preferably comprises

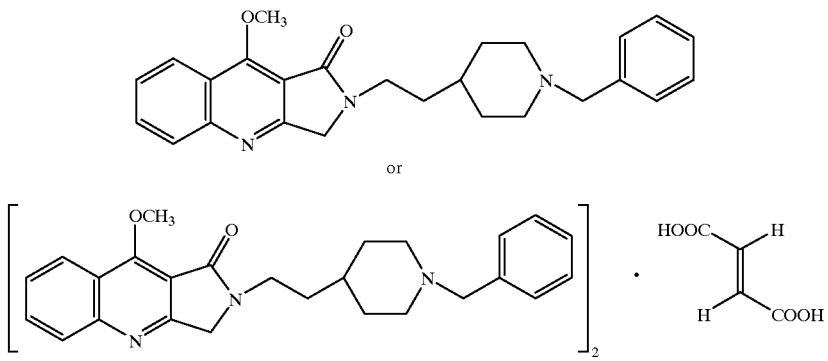

or

DETAILED DESCRIPTION

Figure 1A:
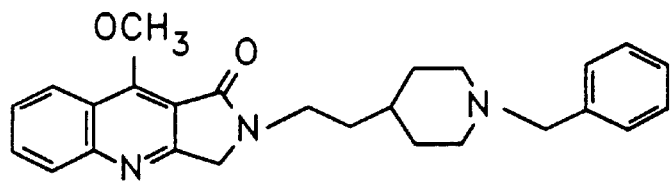
FIG. 1A shows the structure of N-[2-(1-benzylpiperzin-4-yl)ethyl]-2,3-dihydro-9-methoxy-1H-pyrrolo[3,4b]quinolin-1-one.

U.S Pat. Nos. 5,190,951; 5,540,934; and 5,300,517 disclose quinoline derivatives (including salts thereof and piperidine derivatives thereof) useful in inhibiting AChE. These references report that the quinoline derivatives are useful in "preventing or treating dementia" as well as for treatment of individuals "suffering from or under a risk of suffering from dementia." According to the references, senile dementia is broadly classified into the cerebral vascular disorder type and the Alzheimer's type. Processes for preparing these quinoline derivatives are also disclosed in the foregoing patent references, which also report that selected compounds within the quinoline derivative genera evidence anti-AChE activity as well as efficacy in improving amnesia induced by scopolamine. The foregoing patents are incorporated herein, in their entirety, by reference.

It has been discovered in accordance with the present invention that selected compounds within the genera disclosed in the foregoing references, including Cm.A., are also potent antagonists of the 5-HT3 receptor. Antagonists to the 5-HT3 receptor lead, inter alia, to the neuronal release of the neurotransmitter ACh (e.g., Ramirez, supra). 5-HT3 receptors are also located along the lining of the gut, and, as noted above, 5-HT3 receptor antagonists prevent vomiting responses (e.g., Parikh, supra). As those of skill in the art will appreciate, one of the most prevalent side effects associated with AChE inhibitors that have been clinically evaluated, and which have been approved for commercialization in the United States, is vomiting. While with a disease such as AD such side effects may be considered clinically acceptable, if the efficacy of such compounds is marginal then such clinically acceptable side effects may lead to patient-use drop-off. Furthermore, such side-effects may prohibit, for practical reasons, a physician from providing a higher dose of such a drug to a patient.

Thus, a compound that not only has multiple therapeutic modes of action, but may also aid in reducing certain side effects associated with semi-mechanistically similar therapeutics, would provide a substantial improvement in the therapeutic arsenal available to patients and physicians. The compounds described herein, including Cm.A, are such compounds.

In some preferred embodiments, acetylcholine enhancers are provided that have the structure:

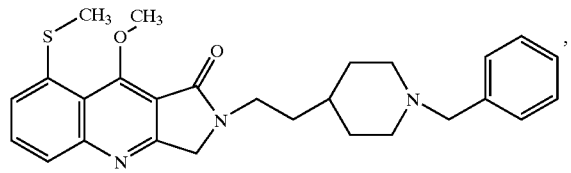

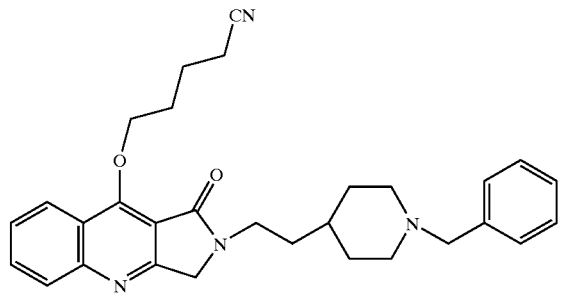

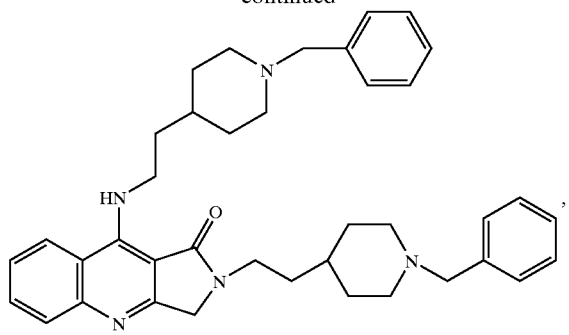

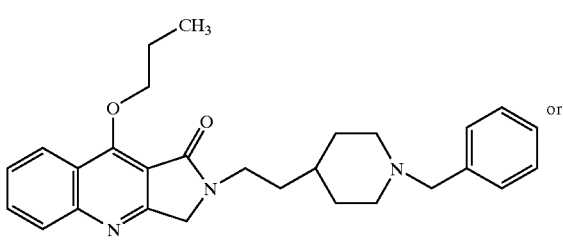

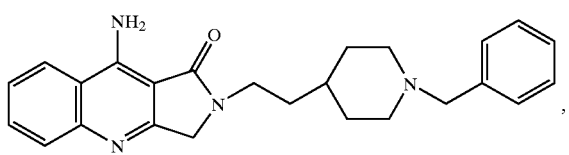

and pharmaceutically acceptable salts of the foregoing compounds. A particularly preferred ACh enhancer is N-[2-(1-Benzylpiperizin-4-yl) ethyl]-2,3-dihydro-9-methoxy-1H-pyrrolo[3,4-b] quinolin-1-one, i.e.,

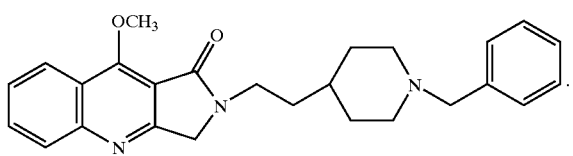

In one particularly preferred embodiments, the acetylcholine enhancer is N-[2-(1-benzylpiperizin-4-yl)ethyl]-2,3-dihydro9-methoxy-1H-pyrrolo [3,4-b] quinolin-1-one heimfumatate, i.e.:

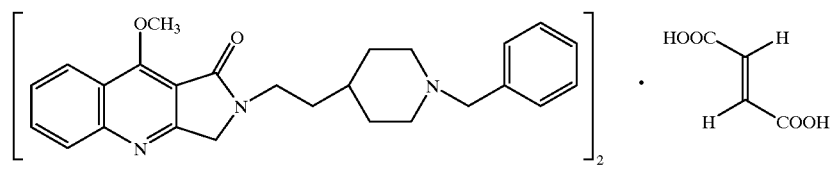

referred to herein as Compound A ("Cm.A.").

Also provided in accordance with the invention are methods for both inhibiting the enzyme acetylcholine esterase, and antagonizing the serotonin 5HT3 receptor in a system that comprises both acetylcholine esterase and the serotonin 5HT3 receptor. In preferred embodiments, the methods comprise introducing to the system an acetylcholine enhancer, preferably selected from the group consisting of compounds of formula:

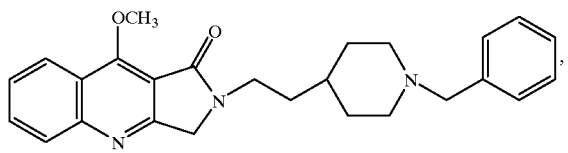

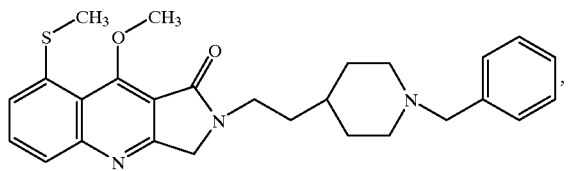

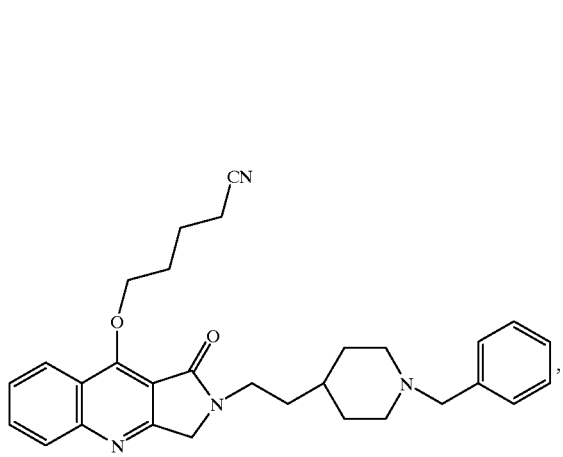

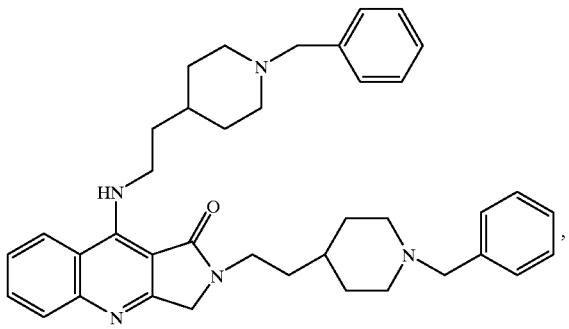

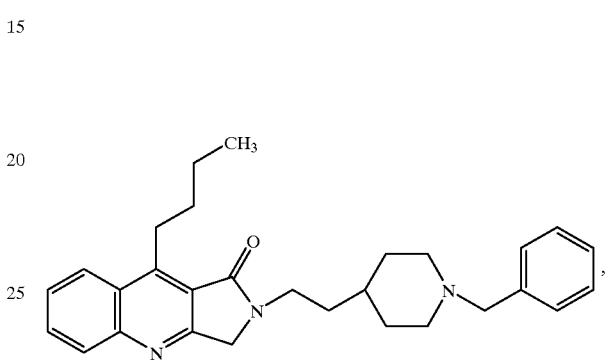

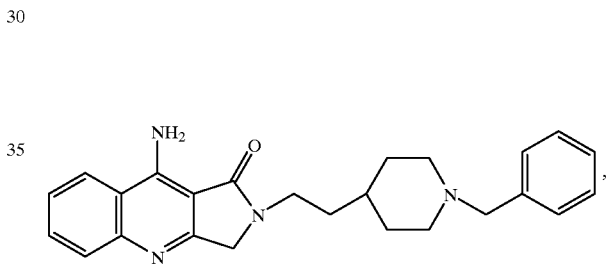

and pharmaceutically acceptable salts thereof.

In some more preferred embodiments, the compound is

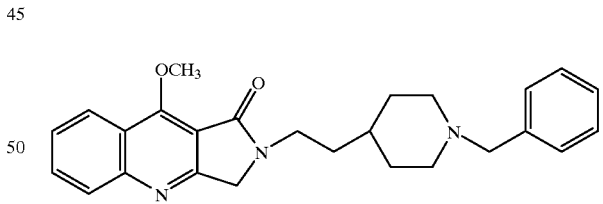

or a pharmaceutically acceptable salt thereof. In even more preferred embodiments, the acetylcholine enhancer has the formula:

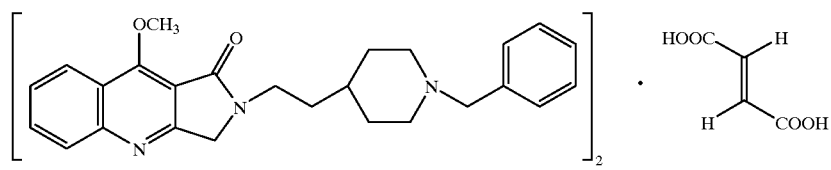

The present invention also provides pharmaceutical compositions comprising acetylcholine enhancers. In preferred embodiments, the pharmaceutical compositions comprise a compound of formula:

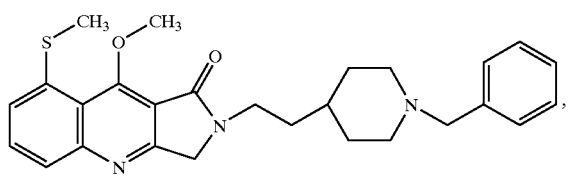,

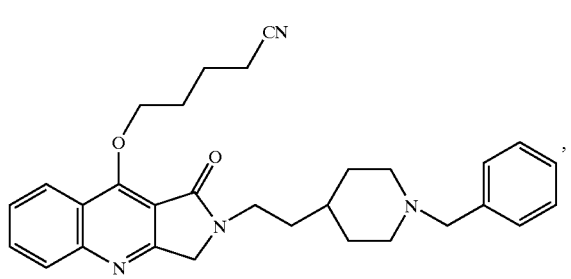,

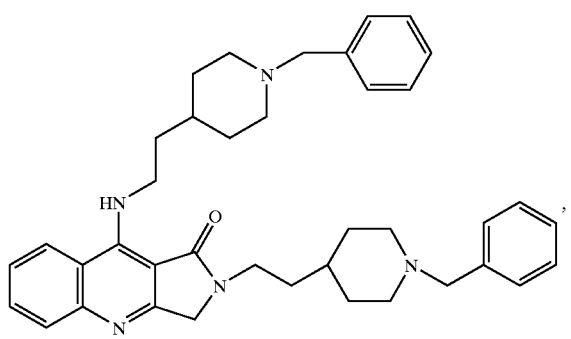,

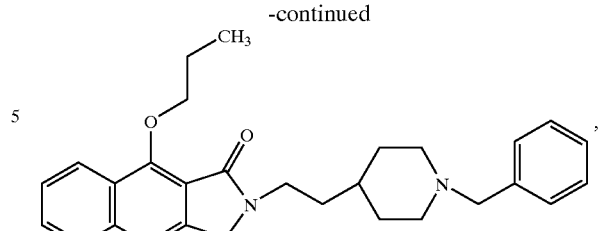,

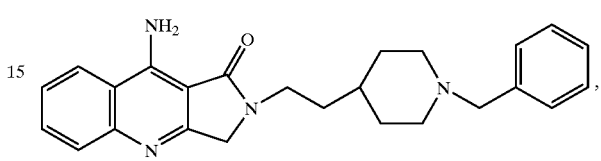, or pharmaceutically acceptable salts thereof.

In further preferred embodiments, the pharmaceutical composition comprises a compound of formula:

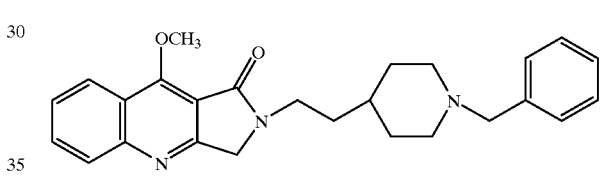

or a pharmaceutically acceptable salt thereof, which is preferably

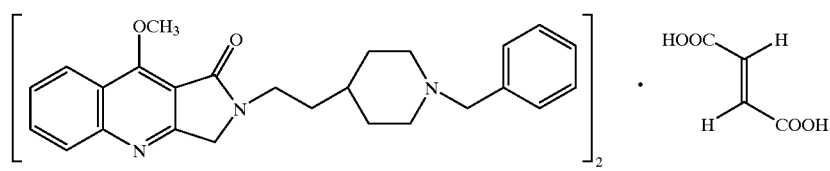

The present invention also provides methods of both inhibiting the enzyme acetylcholine esterase and antagonizing the serotonin 5HT3 receptor comprising providing an individual in need of inhibiting acetylcholine esterase and antagonizing the serotonin 5HT3 receptor with a pharmaceutical composition of the invention, which preferably comprises

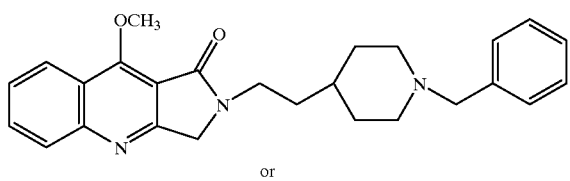

or

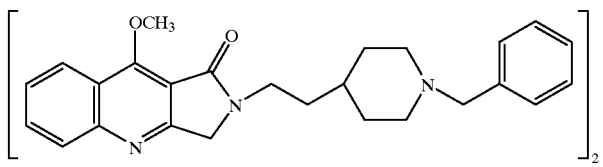 · 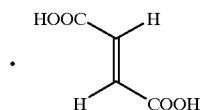

As will be set forth in greater detail below, Cm.A has been demonstrated to be an AChE inhibitor (see Example 2), a 5-HT3 receptor antagonist (which allows for increased release of neuronal ACh) (see Example 4), and as compared with equivalent doses of THA and E2020, Cm.A does not evidence the side effects associated with these two compounds, e.g., vomiting (see Example 1, infra). Because of this duality of mechanistic activity (i.e., AChE inhibition and 5-HT3 receptor antagonism), the compounds of the invention, for example Cm.A, are referred to herein as "acetycholine (ACh) enhancers."

As noted, methodologies for preparing such compounds are disclosed in the above referenced U.S. patents. The pharmaceutically acceptable salts of the compounds described herein include pharmaceutically acceptable acid addition salts, metal salts, ammonium salts, organic amine addition salts, and amino acid addition salts. Examples of the acid addition salts are inorganic acid addition salts such as hydrochloride, sulfate and phosphate, and organic acid addition salts such as acetate, maleate, fumarate, tartrate, citrate and lactate; examples of the metal salts are alkali metal salts such as lithium salt, sodium salt and potassium salt, alkaline earth metal salts such as magnesium salt and calcium salt, aluminum salt, and zinc salt; examples ofthe ammonium salts are ammonium salt and tetramethylammonium salt; examples of the organic amine addition salts are salts with morpholine and piperidine; and examples of the amino acid addition salts are salts with glycine, phenylalanine, glutamic acid and lysine. Hemifumarate salts are particularly preferred.

In accordance with some preferred embodiments of the methods of the invention, compounds or compositions of the invention are introduced to a system that is in need of both inhibiting the enzyme acetylcholine esterase, and antagonizing the serotonin 5HT3 receptor. As used herein, the term "introduce to a system" means placing a desired compound or composition into the system in a manner that is consistent with the active component both causing the inhibition of acetylcholine esterase present in the system, and antagonizing the serotonin 5HT3 receptor present in the system. The term "system" is intended to include both living organisms, particularly mammals, and especially humans, as well as in vitro systems such as diagnostic assays and the like. It will thus be recognized that compounds and compositions of the invention can be introduced to a system by a variety of means. In more preferred embodiments, the system is apatient in need of both inhibiting the enzyme acetylcholine esterase, and antagonizing the serotonin 5HT3 receptor, such as, for example, an AD patient. Thus, "introducing to a system" includes administration to a patient.

Preferred pharmaceutical compositions comprising the disclosed compounds are in the form of tablets; given the nature of, e.g. AD, it is preferred that the therapeutic be administered orally. However, other routes of administration can find use in the methods of the invention. Thus, compounds provided herein can be formulated into pharmaceutical compositions by admixture with pharmaceutically acceptable nontoxic excipients and carriers. As stated previously, while oral administration, particularly in the form of tablets or capsules, is preferred due to the nature of AD, useful compositions also can be prepared for use in parenteral administration, including in the form of liquid solutions or suspensions; intranasally, particularly in the form of powders, nasal drops, or aerosols; or dermally, via, for example, trans-dermal patches.

The compositions of the invention can be conveniently administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for trans-dermal patches are preferably lipophilic emulsions.

The concentrations of the compounds described herein in atherapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. The preferred dosage of drug to be administered is likely to depend on such variables as the type or extent of progression of the disease or disorder, the overall health status of the particular patient, the relative biological efficacy of the compound selected, and formulation of the compound excipient, and its route of administration.

The compounds of this invention can be employed as the sole active agent in a pharmaceutical composition. Alternatively, they can be used in combination with other active ingredients.

The invention is further illustrated by way of the following examples, which are intended to elucidate the invention. These examples are not intended, nor are they to be construed, to limit the scope of the disclosure, or the claims to follow.

EXAMPLES

For the following examples, the compounds were supplied by SSP Company (formerly SS Pharmaceuticals, Co., Tokyo, Japan).

Example 1

Hepatotoxic Analysis

A. Two-Week Study

Cynomologous monkeys were orally administered 5 mg/kg/day of Cm.A, THA or E2020 once a day for 2 weeks to investigate and compare their respective hepatotoxicity properties. The following parameters were examined: body weight, clinical signs, food consumption, blood biochemistry (GOT, GPT, ALP, LDH, γ-GTP, ChE, Bil, T.Pro, Alb, A/G ratio, T.Cho, NEFA, TG). After the administration period, the animals were sacrificed and autopsied. Organs and tissues were weighed, then examined histopathologically.

During the dosing period, THA and E2020 caused vomiting and soft stools (or diarrhea) sporadically; Cm.A also caused soft stools, but to a lesser extent than the other two compounds. Decreases in food consumption and body weight were evident in monkeys dosed with E2020. Changes in blood biochemical parameters induced by dosing were evident by increases in ALP and TG in the THA-group, and increases in LDH, T. Cho, NEFA and TG in the E2020group. No substantial changes were determined from autopsy, organ weight determination and histopathological examination in all the dosing groups. Results are summarized in Table 1.

TABLE 1

Hepatoxic summary for Cm.A, THA and E2020 (oral dosing - 2 weeks)

| | Cm.A | | THA | | E2020 | |
|---|---|---|---|---|---|---|
| Observations | M | F | M | F | M | F |
| Clinical signs | | | | | | |
| vomiting | – | – | + | + | – | + |
| softstool | + | + | – | – | ++ | – |
| Food consumption | – | – | – | – | ↓ | – |
| Body weight | – | – | – | – | ↓ | – |
| Blood biochemistry | – | – | ↑: ALP | ↑: TG | ↑: LDH T.Cho NEFA TG | ↑: TG |
| Autopsy, | | | | | | |
| organ weight and histopathology | – | – | – | – | – | – |

– no remarkable change
↑ increase
↓ decrease
+ slight
++ severe (diarrhea)

These results support the position that Cm.A has a lower overall toxicity profile as compared with THA and E2020, and that Cm.A evidences no hepatotoxicity.

B. Four-Week Study

Cm.A, THA or E2020 was given by oral administration for four (4) weeks to cynomologous monkeys. During the testing period, these animals were dosed with three different regimens: first, animals were dosed with 10 mg/kg/day for 7 days, followed by 32 days-washout period, second, animals were dosed with 5 mg/kg/day for 14 days, and thereafter the animals were dosed with 10 mg/kg/day for 7 days. The following parameters were examined: body weight, clinical signs, food consumption, blood biochemistry (GOT, GPT, ALP, LDH, γ-GTP, ChE, Bil, T.Pro, Alb, A/G ratio, T.Cho, NEFA, TG).

The animals treated with THA and E2020 evidenced severe vomiting and soft stools or diarrhea were observed, decrease in body weight and food consumption, and changes in certain blood biochemical tests (increase in TG and NEFA, decrease in ChE and T.Cho) were also evident. Animals treated with Cm.A exhibited minimal adverse clinical signs and no remarkable change in food consumption and body weight. A small increase in TG was observed in the Cm.A treated animals. Results are summarized in Table 2.

TABLE 2

Hepatoxic summary for Cm.A, THA and E2020 (oral dosing - four weeks)

| | CM.A | | THA | | E2020 | |
|---|---|---|---|---|---|---|
| Observations | M | F | M | F | M | F |
| Clinical signs | | | | | | |
| vomiting | – | – | +++ | +++ | +++ | +++ |
| soft stool | – | ± | +++ | +++ | +++ | +++ |
| Food consumption | – | – | ↓ | ↓ | ↓ | ↓ |
| Body weight | | | ↓ | ↓ | ↓ | ↓ |
| Blood biochemistry | ↑: TG | ↑: TG | ↑: TG NEFA ↓: CHE T.Cho | ↑: TG NEFA | ↑: TG NEFA | ↑: TG NEFA |

– no remarkable change
↑ increase
↓ decrease
± a few times
+++ many times

These results support the position that at equivalent doses, Cm.A exhibited fewer toxic signs than THA and E2020 in the parameters tested.

Example 2

Inhibitory Effect on Acetylcholinesterase Activity

Wistar rats were orally administered with Cm.A, THA or E2020. After 1 hour, rats were sacrificed and brains were isolated and divided into several portions. AChE activity in preparations from hippocampus, striatum, frontal cortex and parietal cortex was determined by Ellman's method. See, Ellman, G. L., et al., 7 Biochem. Pharmacol. 88 (1961). Results are summarized in Table 3.

TABLE 3

Effects of Cm.A, THA and E2020 on AChE activity at various brain regions

| | Dose | | AChE activity (nmol/min/mg protein | | |
|---|---|---|---|---|---|
| Drugs | (mg/kg, p.o) | N | Hippocampus | Striatim | Frontal cortex | Parietal cortex |
| Control | | 8 | 47.7 ± 1.8 | 264.1 ± 20.0 | 59.4 ± 4.0 | 31.9 ± 2.6 |
| Cm.A | 1 | 6 | 37.6 ± 0.8** | 238.9 ± 5.4 | 48.1 ± 2.5* | 27.3 ± 0.5* |
| | 3 | 6 | 42.1 ± 1.3 | 219.9 ± 10.0 | 56 ± 3.0 | 31.3 ± 1.6 |
| | 10 | 6 | 48.3 ± 2.9 | 274.0 ± 26.0 | 58.4 ± 4.5 | 32.6 ± 1.7 |
| E2020 | 10 | 5 | 36.4 ± 1.9** | 249.3 ± 12.0 | 40.5 ± 5.4** | 25.2 ± 1.1* |
| THA | 10 | 5 | 35.1 ± 1.7** | 273.8 ± 6.2 | 44.5 ± 3.8* | 24.1 ± 0.5* |

*, **$P < 0.05, 0.01$ vs control

The results of Table 3 support the position that THA and E2020 evidenced inhibition of AChE activity in hippocampus at a rather high dose, and that Cm.A showed inhibition of AChE in a nondose dependent manner (i.e., at all tested doses).

Example 3

Acetylcholine Release

A. Effect on ACh Release in Striatum

ACh content in perfusate obtained from striatum (Bregma, A: 0.2 mm, L: 3.0 mm, H: 4.0 mm) of brain were continuously detected by means of HPLC and ECD through the microdialysis system using freely moving rats. See Messamore, E., et al, 32 *Neuropharmacol.* 291 (1993) and Kawashima, K., et al, 350 Naunyn-Schmiedeberg's *Arch. Pharmacol.* 523 (1994). After an equilibration period of more than 2 hours, five fractions were allowed to obtain basal ACh content. Compounds were injected i.p., and thereafter, a microdialytic analysis was conducted for 3 hours. Results are summarized in FIG. 2.

In young rats (2 month-old Wistar), Cm.A (10, 30 mg/kg) increased ACh content in perfusate dose-dependently up to 131% and 369%, respectively. Despite these increases, few centrally acting cholinergic symptoms (e.g. tremor, chewing and yawning) were evident (data not shown). On the other hand, THA and E2020, which both increased the ACh content more potently and long-lastingly than Cm.A, also evidenced the foregoing cholinergic symptoms, but with greater severity as compared with Cm.A (data not shown).

Figure 2A:
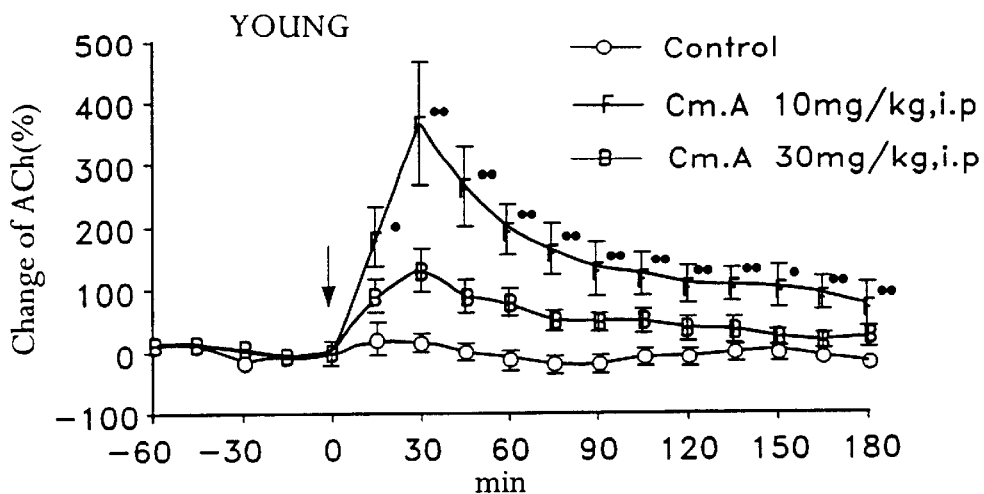
FIGS. 2A–F provide graphic results of the effects of Cm.A, tacrin ("THA") and E2020 on extracellular levels of ACh in microdialysis samples from striatum of conscious, freely moving young (2A, 2C, 2E) and aged (2B, 2D, 2F) rats. Compounds were administered at 0 min (i.p., arrow symbol). Control animals were injected with saline (i.p.). Each point represents the mean with S.E.M. (N=4–6)*,**: $P<0.05$, $0.01$ vs. control.
Figure 2B:
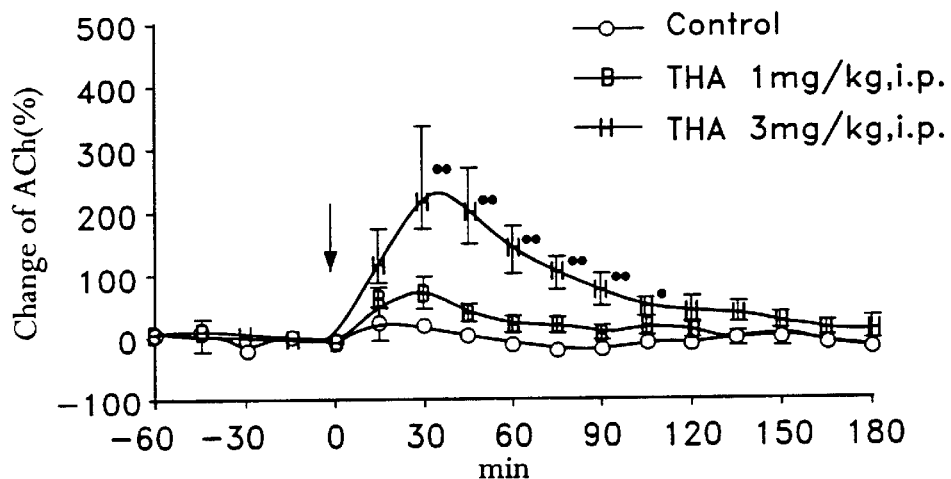
Figure 2C:
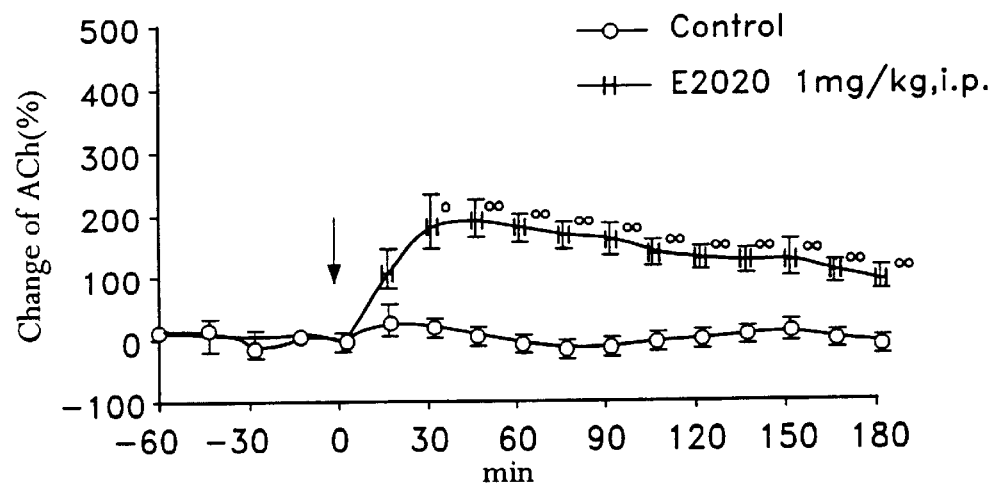
Figure 2D:
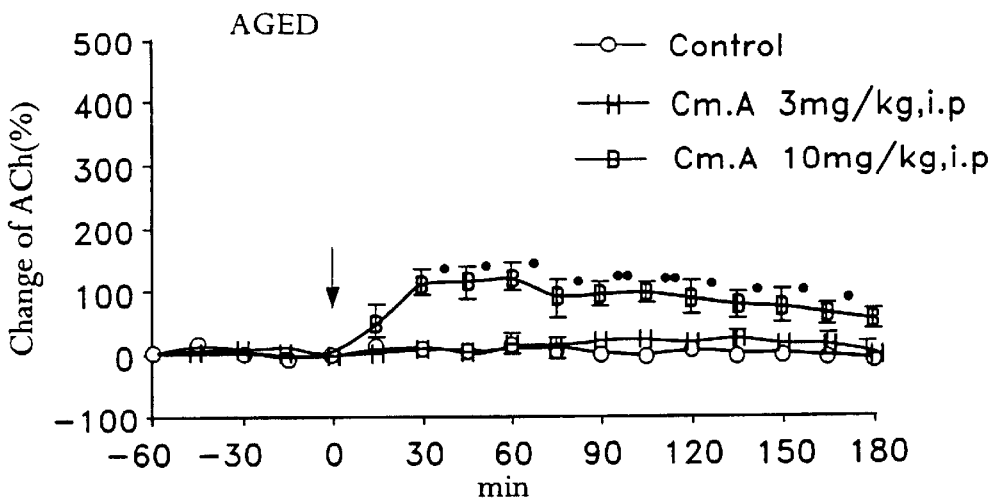
Figure 2E:
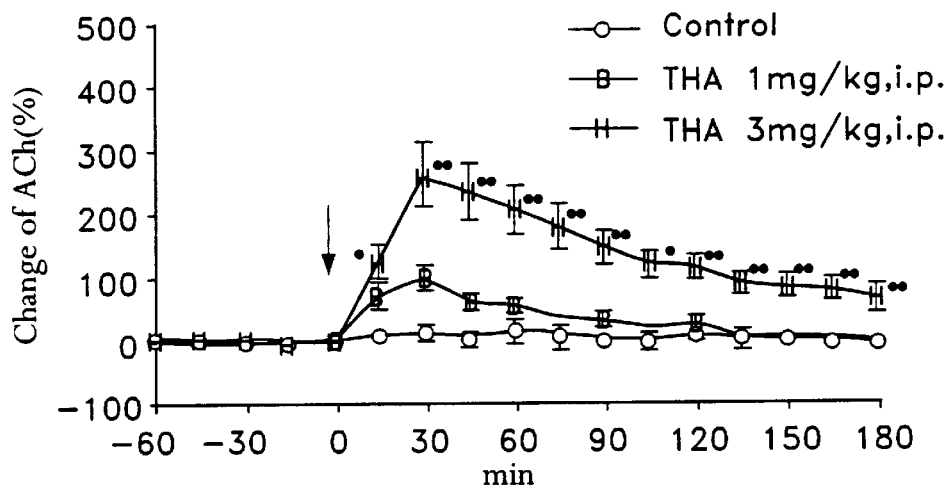
Figure 2F:
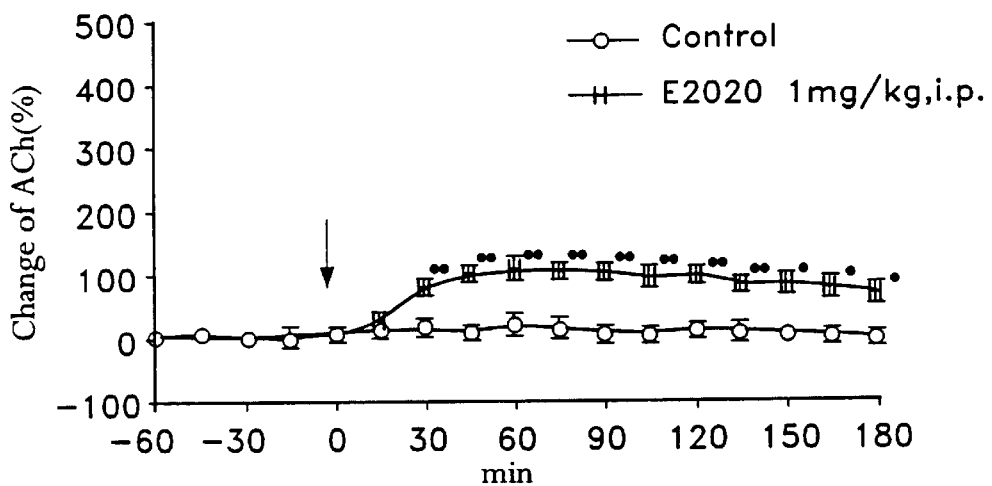

In aged rats (25~27 month-old Fischer 344), similar increases which were evidenced in young rats were also obtained, but with somewhat longer duration of action than young rats. The lower potency of E2020 in aged rats relative to young rats may be due to higher pre-treatment level of ACh (FIG. 2F). Except for E2020-treated aged rats, basal ACh levels in striatum were approximately the same between young Wistar and young and aged Fischer 344 rats.

B. Effect on ACh Release in Hippocampus

Figure 3A:
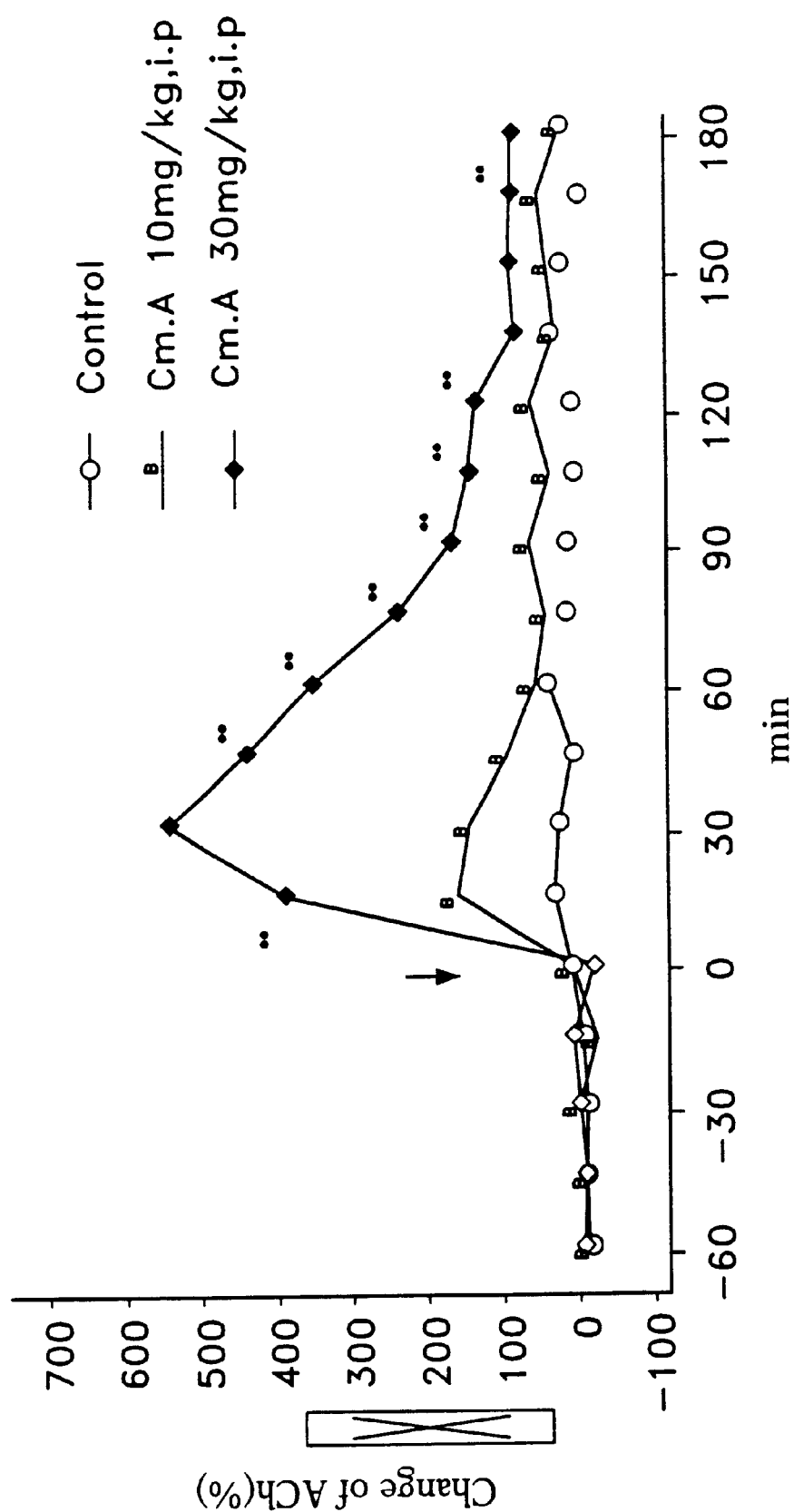
FIGS. 3A–C provide graphic results of the effects of Cm.A (3A), THA (3B) and E2020 (3C) on extracellular levels of ACh in microdialysis samples from hippocampus of conscious, freely movingrats. Compounds were administered at 0 min (i.p, arrow symbol). Control animals were injected with saline (i.p.). Each point represents the mean with S.E.M. (N=6)*,**: $P<0.05$, $0.01$ vs. control.
Figure 3B:
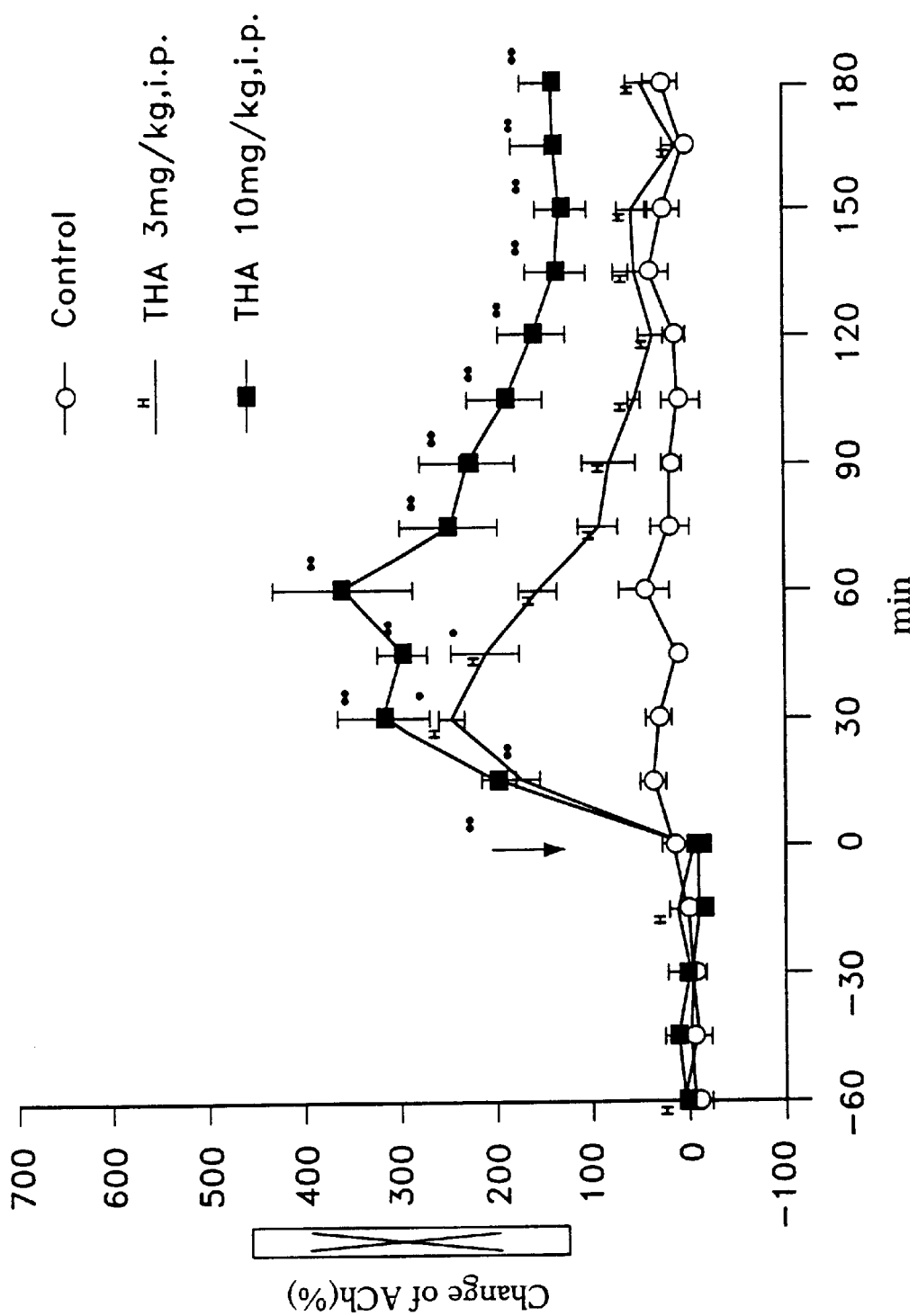
Figure 3C:
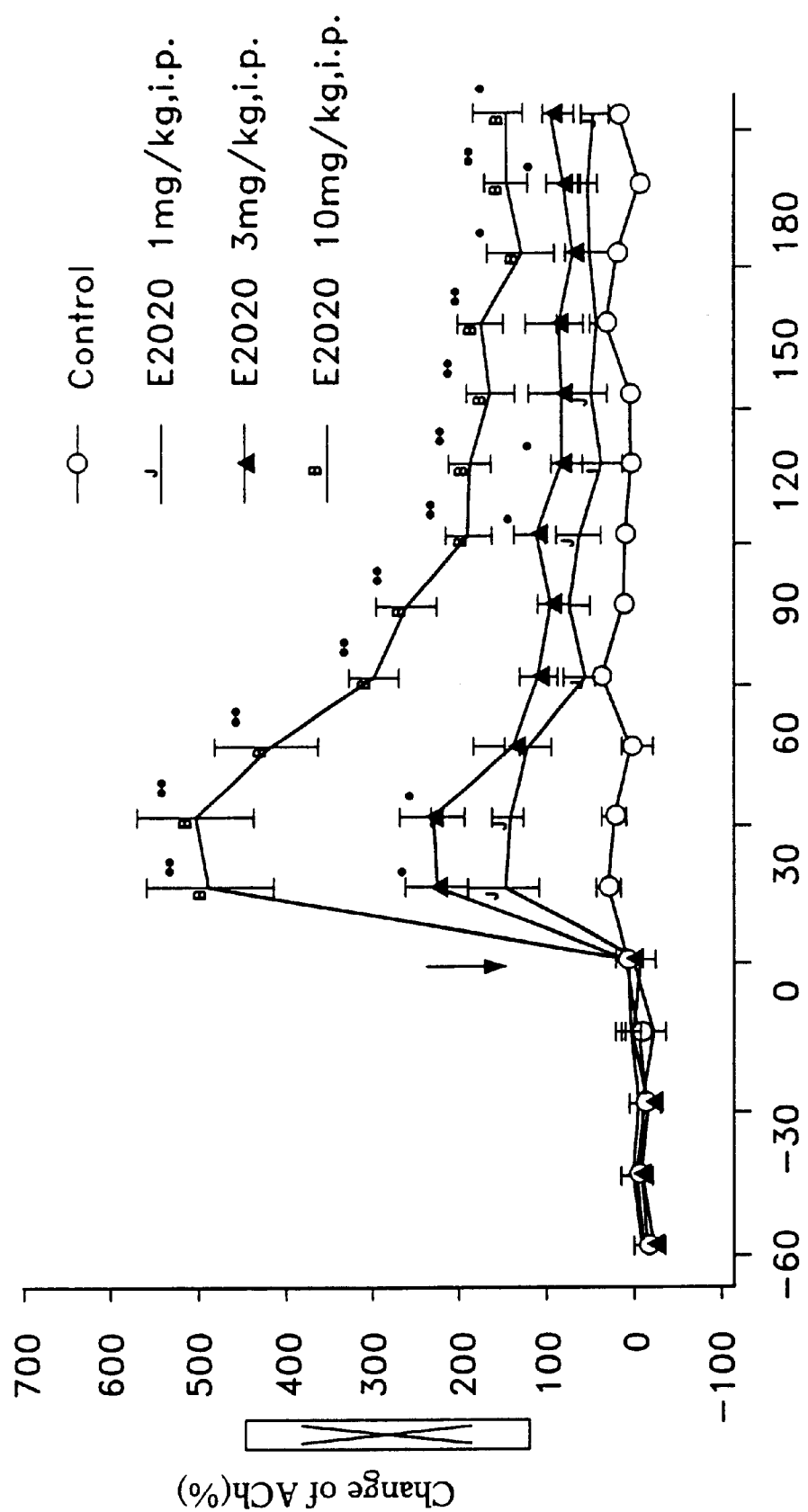

ACh content in perfusate obtained from hippocampus (Bregma, A: −5.8 mm, L: 5.0 mm, H: 4.0 mm) of brain were continuously detected by means of HPLC and ECD through the microdialysis system using freely moving rats (See Messamore and Kawashima, supra). After an equilibration period, five fractions were allowed to obtain basal ACh content. Test substances were injected i.p., and thereafter, microdialytic analysis was conducted for 3 hr. Results are summarized in FIG. 3.

Cm.A (10, 30 mg/kg) increased the ACh content in perfusate in a dose-dependent fashion, 164% and 552%, respectively. Few centrally acting cholinergic symptoms (e.g. tremor, chewing and yawning) were observed (data not shown). THA and E2020 also increased ACh content similar to that observed with Cm.A, but the effects of THA were somewhat weak. Moreover, concomitantly with this increase, cholinergic symptoms as discussed in Example 3A were more apparent as compared with Cm.A.

Example 4

5HT3 Receptor

A. In Vivo Study—Antagonistic Action on Peripheral 5-HT3 Receptor

Figure 4A:
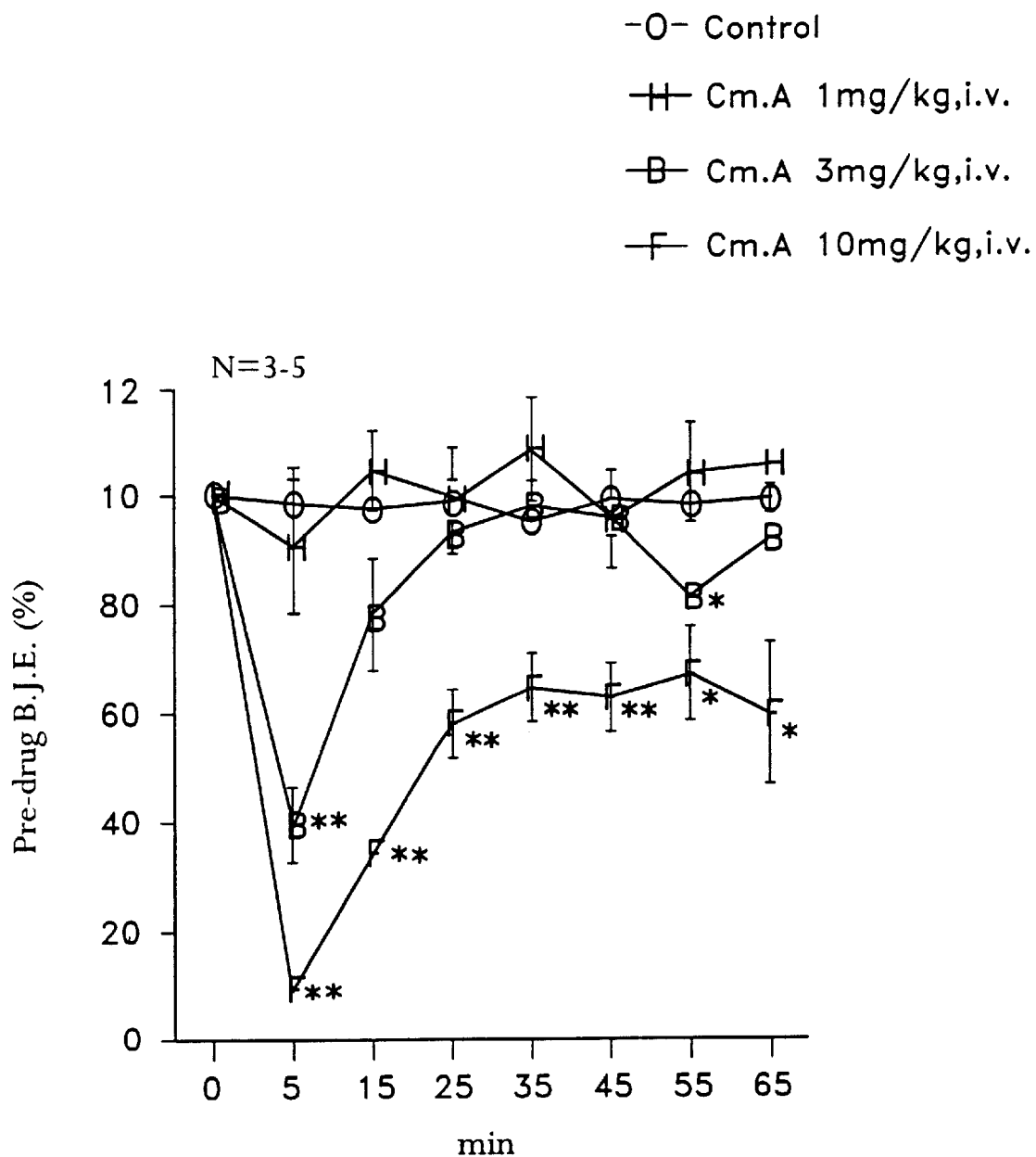
FIGS. 4A–B provides graphic results of the inhibitory effects of Cm.A (4A) and THA (4B) on 5-HT-evoked von Bezold-Jarish Effect ("BJE") in anesthetized rats. A bolus dose of serotonin was injected every 10 minutes. Each point represents the mean with S.E.M. *, **: $P<0.05$, $0.01$ vs. control.
Figure 4B:
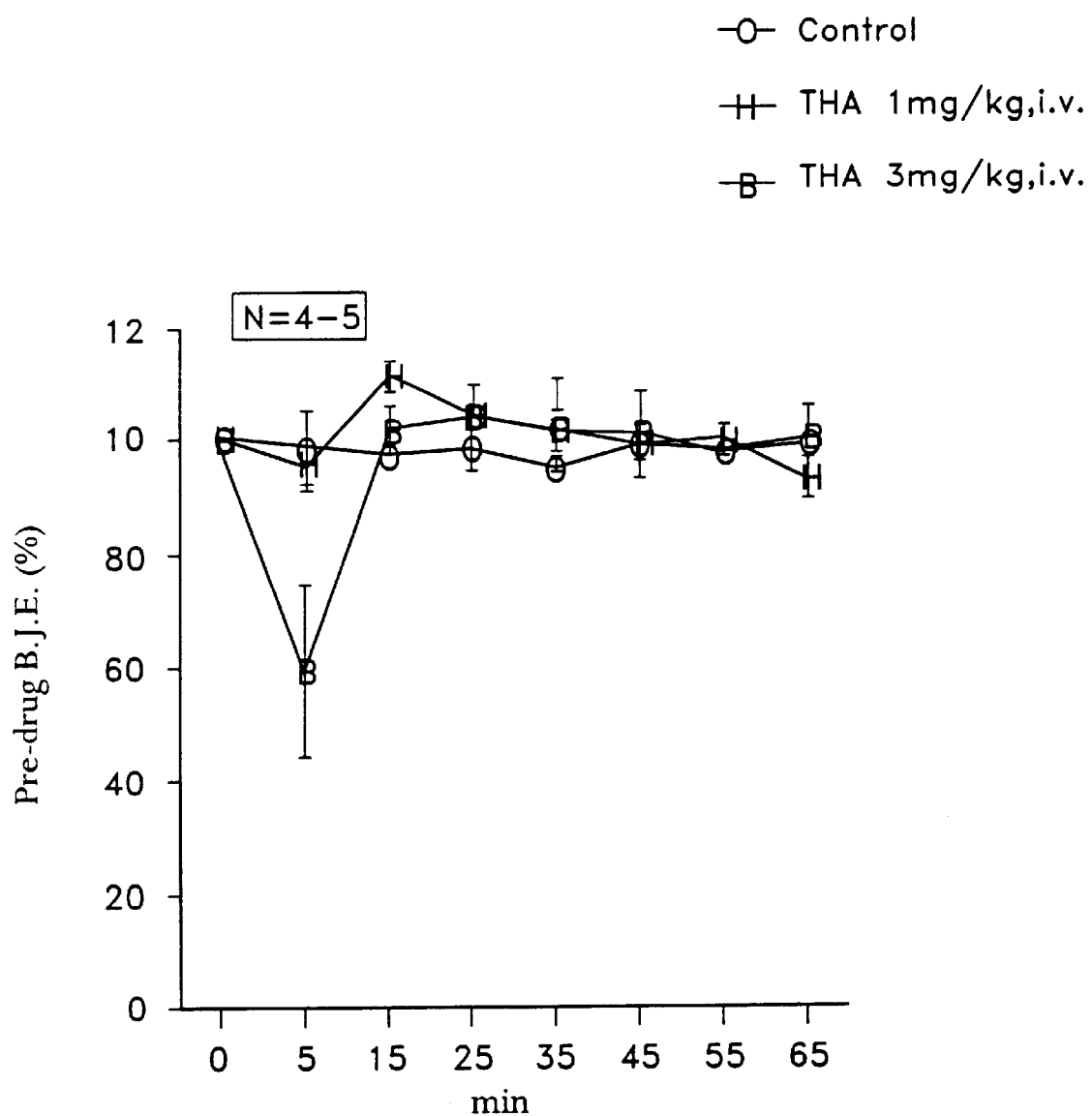

A bolus i.v. injection of serotonin (5-HT) (20 μg/kg) caused reflex bradycardia transiently (von Bezold—Jarish Effect: B.J.E.) via activation of peripheral 5-HT3 receptor in anesthetized rats. The effect of Cm.A, THA and E2020 on peripheral 5-HT3 receptor were tested using B.J.E. as a model. Results are summarized in FIG. 4.

Pretreatment with Cm.A inhibited B.J.E. dose dependently (3 to 10 mg/kg, i.v.) without any change on blood pressure and heart rate (data not shown). THA evidenced a slight tendency to decrease the reflex, but THA caused severe hypertension, salivation and tremor at 10 mg/kg (data not shown). E2020 (0.1~1 mg/kg, i.v.) evidenced no inhibitory effect on B.J.E., and E2020 caused hypertension, salivation and tremor at a higher dose than 1 mg/kg, i.v.(data not shown).

B. In Vitro Study—$IC_{50}$ Determination

Binding affinity of a variety of compounds, including Cm.A, for the 5-HT3 receptor was investigated using a commercially available serotonin 5-HT3 binding assay (NovaScreen, Hanover, Md.). The receptor source was NIE-115 cells (See Lunnis, S. C. R. and Kilparick, G. J., 189: *Evr. Jrnl. Pharmacol.* 223 (1990); and Hoyer, D. and Heijt, H. C., 33 *Mol. Pharmacol.,* 303 (1988)). The reference compound utilized was "MDL 72222," a 5-HT3 receptor antagonist. Reactions were carried out in 20 mM HEPES (pH 7.4) containing 150 mM NaCl at 25° C. for 60 minutes. The reaction was terminated by rapid vacuum filtration onto glass fiber filters. Radioactivity trapped onto the filters was determined and compared with the control values.

Under the foregoing conditions, Cm.A was determined to have an $IC_{50}$ of $1.18 \times 10^{-6}$ (MDL 72222 was comparatively determined to have an $IC_{50}$ of $1.74 \times 10^{-8}$). Cm.A was determined to have a Ki of $5.52 \times 10^{-7}$ under the foregoing conditions (MDL 72222 was comparatively determined to have a Ki of $8.15 \times 10^{-9}$). Table 4 sets forth comparative values of $IC_{50}$ and Ki values for a variety of analogues of and compounds related to Cm.A (as determined using the same protocol as defined above for Cm A):

TABLE 4

| Compound | $IC_{50}$ | Ki |
| --- | --- | --- |
| MDL 72222 (Reference Compound) | $8.99 \times 10^{-9}$ | $4.14 \times 10^{-9}$ |
| Cm. B | $1.09 \times 10^{-1}$ | $5.01 \times 10^{-8}$ |
| Cm. C | $2.16 \times 10^{-7}$ | $9.94 \times 10^{-8}$ |
| Cm. D | $4.69 \times 10^{-7}$ | $2.15 \times 10^{-7}$ |
| Cm. E | $2.88 \times 10^{-7}$ | $1.32 \times 10^{-7}$ |
| Cm. F | $3.90 \times 10^{-7}$ | $1.79 \times 10^{-7}$ |
| Cm. G | $2.92 \times 10^{-7}$ | $1.34 \times 10^{-7}$ |

The IC50 value for Cm. B and Cm D (210 nM and 83 nM, respectively; as determined using the protocols set forth in the above-referenced patents) are comparable to the value for Cm. A. See FIGS. 14A through 14F for structures of Cm. B through Cm. G, respectively.

C. Ex Vivo Binding of 5HT3 Receptors

Animals:

Animals (Sprague-Dawley rats) were injected intraperitoneally with 10 mg/kg Cm. A (in 90% ethanol, 10% water, vehicle) (n=3) or vehicle (n=3). After thirty minutes animals were sacrificed and brains were rapidly dissected and frozen in isopentane maintained at −42° C. Sections (horizontal and coronal) were prepared on a cryostat and maintained at −20° C.

Autoradiography:

Brain sections were removed from storage and thawed at room temperature for 30 minutes. Total 5HT3 receptor binding was measured in sections incubated with 0.5 nM ($^3$H)-zacopride (Amerhsam; zacorpide is a 5-HT3 selective ligand) in 50 mM HEPES/TRIS buffer. Nonspecific binding was determined in adjacent sections incubated in the presence of radioligand and 500 nM 5-HT. After a 10 minute incubation at room temperature, sections were washed in icecold buffer (2×1 minute) followed by a 10 second rinse in ice-cold distilled water. Sections were then dried in a stream of cold air overnight. After drying, sections were exposed to x-ray film (Kodak Hyperfilm) and exposed for 4 months.

Analysis

Figure 15:
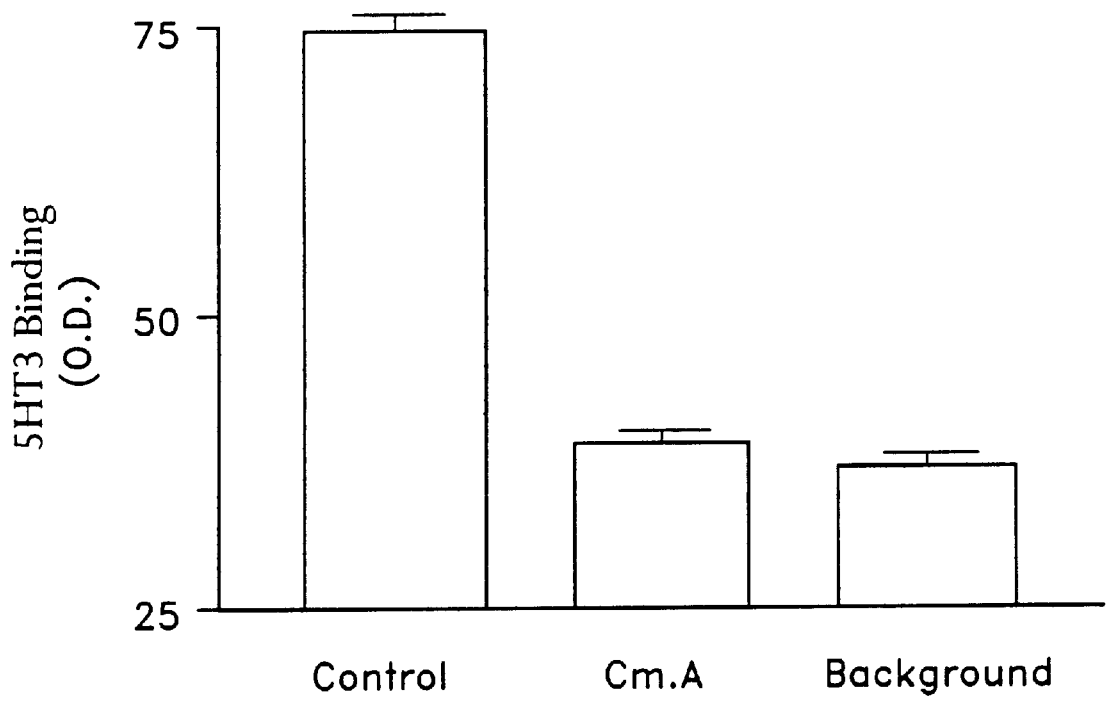
FIG. 15 is a bar graph summarizing the results of IP injection of Cm.A in animals to determine the ability of the compound d to bind to 5HT3 receptor.

Autoradiograms were quantified using an automated image analysis system, DAGE camera IMAGE software. Mean optical density measurements were obtained from four individual measurements per group, control (vehicle injected) and Cm. A; background measurements were obtained from an area of x-ray on which no tissue was exposed. Measurements were made in aregion of the brain referred to as the "amygdala." Results are presented in bar-graph format in FIG. 15. These results support the position that Cm. A occupies 5HT3 receptor sites within the brain, as evidenced by the inability of the radiolabeled 5HT3 selective ligand to be detected in the comparative brain sections.

Example 5

Anti-Amnestic Studies

A. Passive Avoidance

Using male Wistar rats, passive-avoidance studies were conducted using a step through-type, 2 compartment (light and dark) box. In the acquisition trial, at the time when the animal entered the dark area, a guillotine door was closed and an electric shock (0.5~0.8 mA for 3 seconds) was delivered to the animal. After 24 hours, the retention trial was conducted: the rat was put in the light area and the time until the animal entered the dark area (latency) was measured. Cutoff latency was set at 600 seconds. Test substances were orally administered 30 minutes before the acquisition trial.

1. Scopolamine-Induced Memory Impairment

Figure 5:
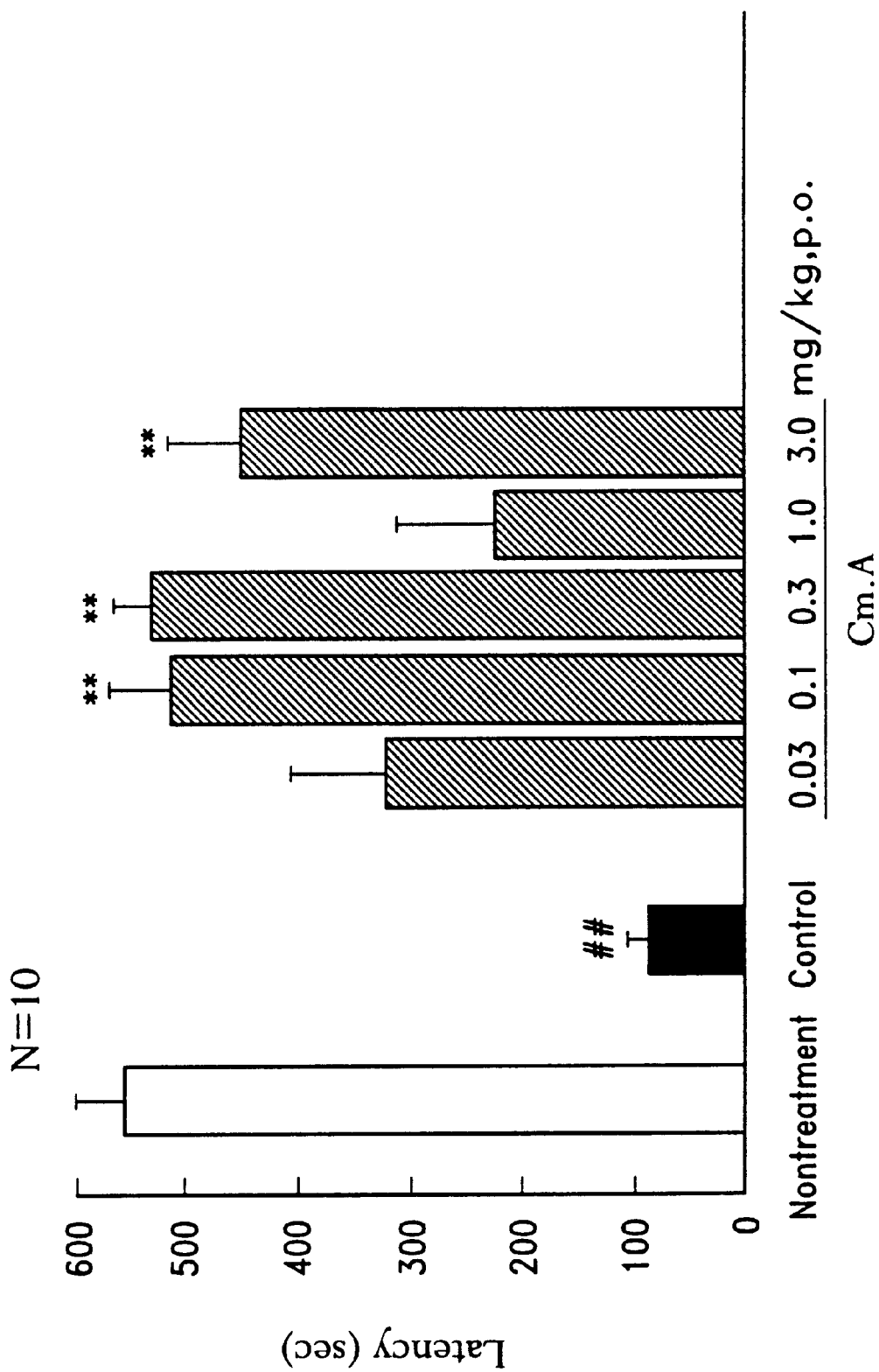
FIG. 5 provides graphic results of the effects of Cm.A on scopolamine-induced amnesia in a passive avoidance task. Each column represents the mean with S.E.M. ##: $P<0.01$ vs. nontreatment. **: $P<0.01$ vs. control.

Rats were treated i.p. with scopolamine (0.5 mg/kg) 15 minutes before the acquisition trial. Scopolamine shortened the latency significantly compared to the non-treated control. Cm.A significantly reversed the effect of scopolamine at doses of 0.1, 0.3 and 3.0 mg/kg. Results are summarized in FIG. 5.

2. Cycloheximide-induced Memory Impairment

Figure 6:
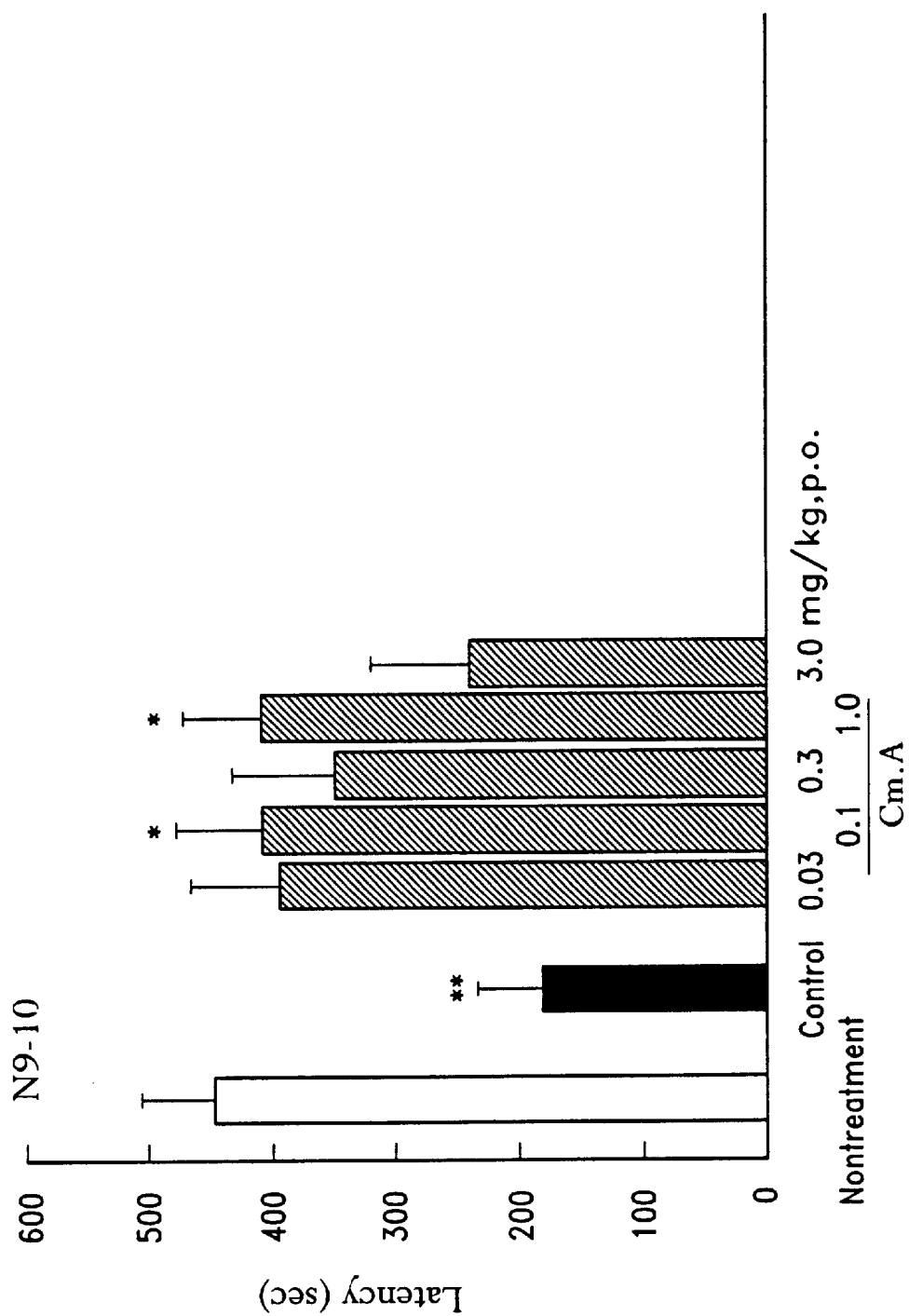
FIG. 6 provides graphic results of the effects of Cm.A on cycloheximide-induced amnesia in a passive avoidance task. Each column represents the mean with S.E.M. ##: $P<0.01$ vs. nontreatment. *,**: $P<0.05$, $0.01$ vs. control.

Rats were treated s.q. with cycloheximide (1.5 mg/kg), a protein synthesis inhibitor, immediately after the electric shock. Cycloheximide also shortened the latency significantly compared with anontreated control. Cm.A prolonged the shortened latency induced by cycloheximide in a non-dose dependent manner. Results are summarized in FIG. 6.

3. Basal Forebrain (BF) Lesion-Induced Memory Impairment

Using the stereotaxic atlas of Paxinos, G. and Watson, C: *The Rat Brain in Stereotaxic Coosrdinates*, $2^{nd}$. Edition, Academic Press, San Diego, Calif. (1986), basal forebrain (Bregma, A: 1.4 mm, L: ±2.6 mm, H: −7.0 mm) was bilaterally identified and a pair of microsyringes inserted therein, through which ibotenic acid (7.5 $\mu$g each) was infused to denervate the region. After 2 weeks, the acquisition trial was conducted. Effects of Cm.A, THA and E2020 were determined after single or repeated doses.

Figure 7:
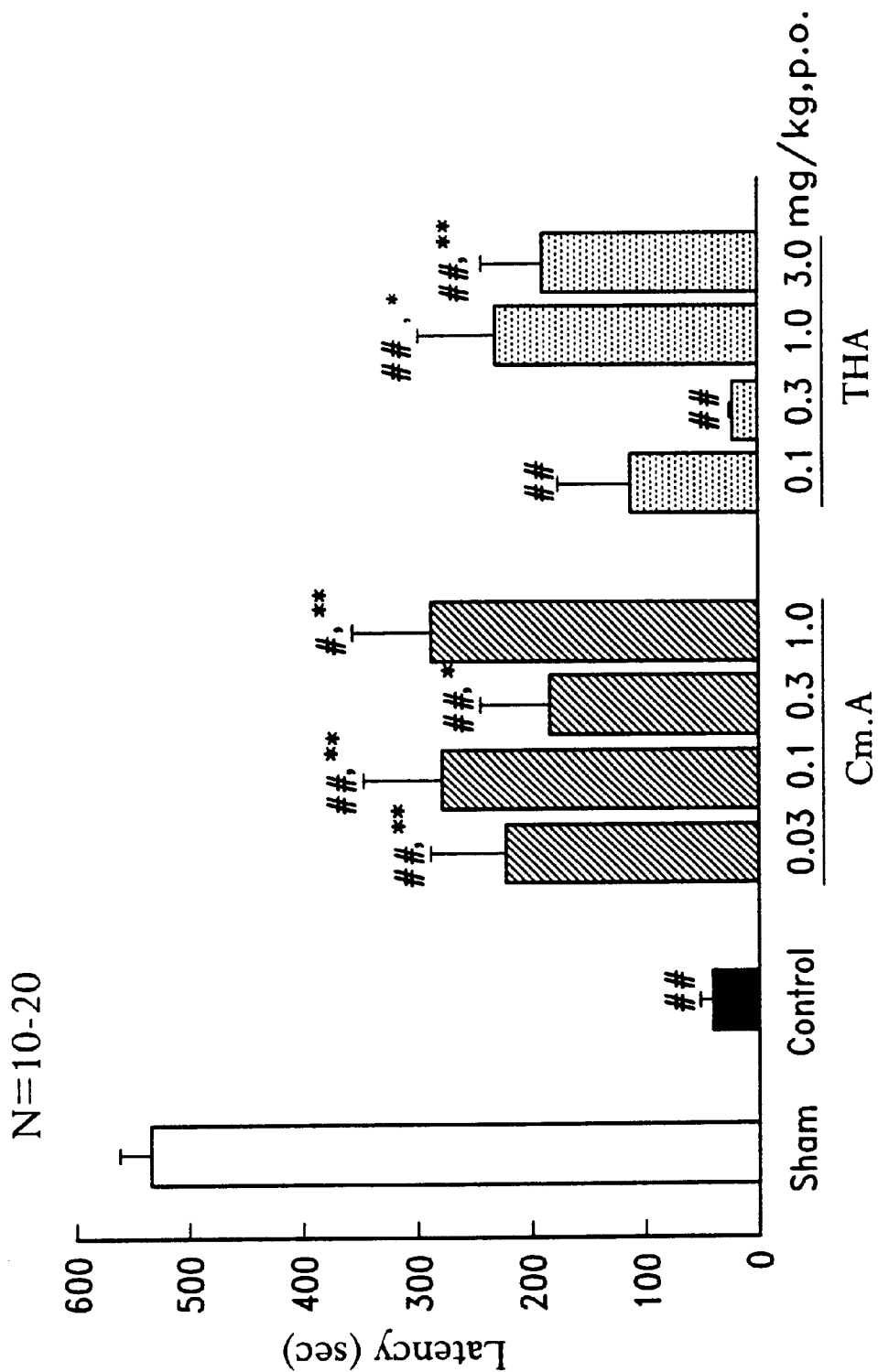
FIG. 7 provides graphic results of the effects of single treatment with Cm.A and THA on memory deficit induced by BF-lesion in a passive avoidance task. Each column represents the mean with S.E.M. #, ##: $P<0.05$, $0.01$ vs. sham. *,**: $P<0.05$, $0.01$ vs. control.
Figure 8:
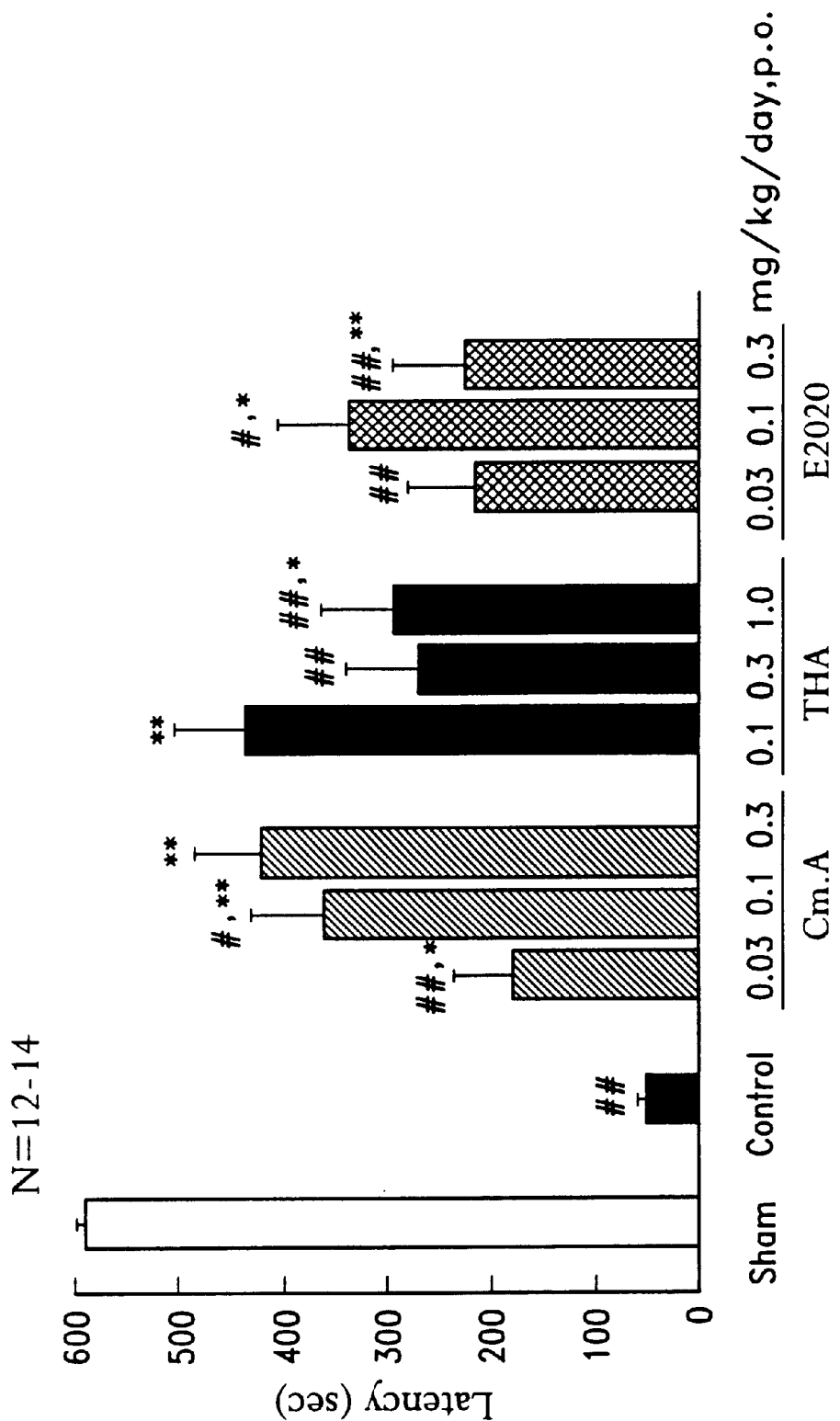
FIG. 8 provides graphic results of the effects of repeated treatment with Cm.A, THA and E2020 on memory deficit induced by BF-lesion in a passive avoidance task. Each column represents the mean with S.E.M. #, ##: $P<0.05$, $0.01$ vs. sham. *, **: $P<0.05$, $0.01$ vs. control.

Cm.A decreased the latency of BF-lesioned rats. A single dose of Cm.A (0.03~1.0 mg/kg) partially, but significantly, recovered the memory deficit induced by BF-lesion. See FIG. 7. Furthermore, the results summarized in FIG. 8 support the position that repeated doses of Cm.A (0.03~0.3 mg/kg/day) for 1 week evidenced improvement in recovery as potently as or more potently than THA and E2020.

B. Eight-Arm Radial Maze

Using male Wistar rats, the anti-amnestic effects of Cm.A on spatial cognition was evaluated using an eight-arm radial maze task. After repeated trials for spatial cognition, memory-established rats (which had more than 7 correct choices and less than one error) were utilized.

1. Scopolamine-Induced Deficit in Spatial Memory

Figure 9:
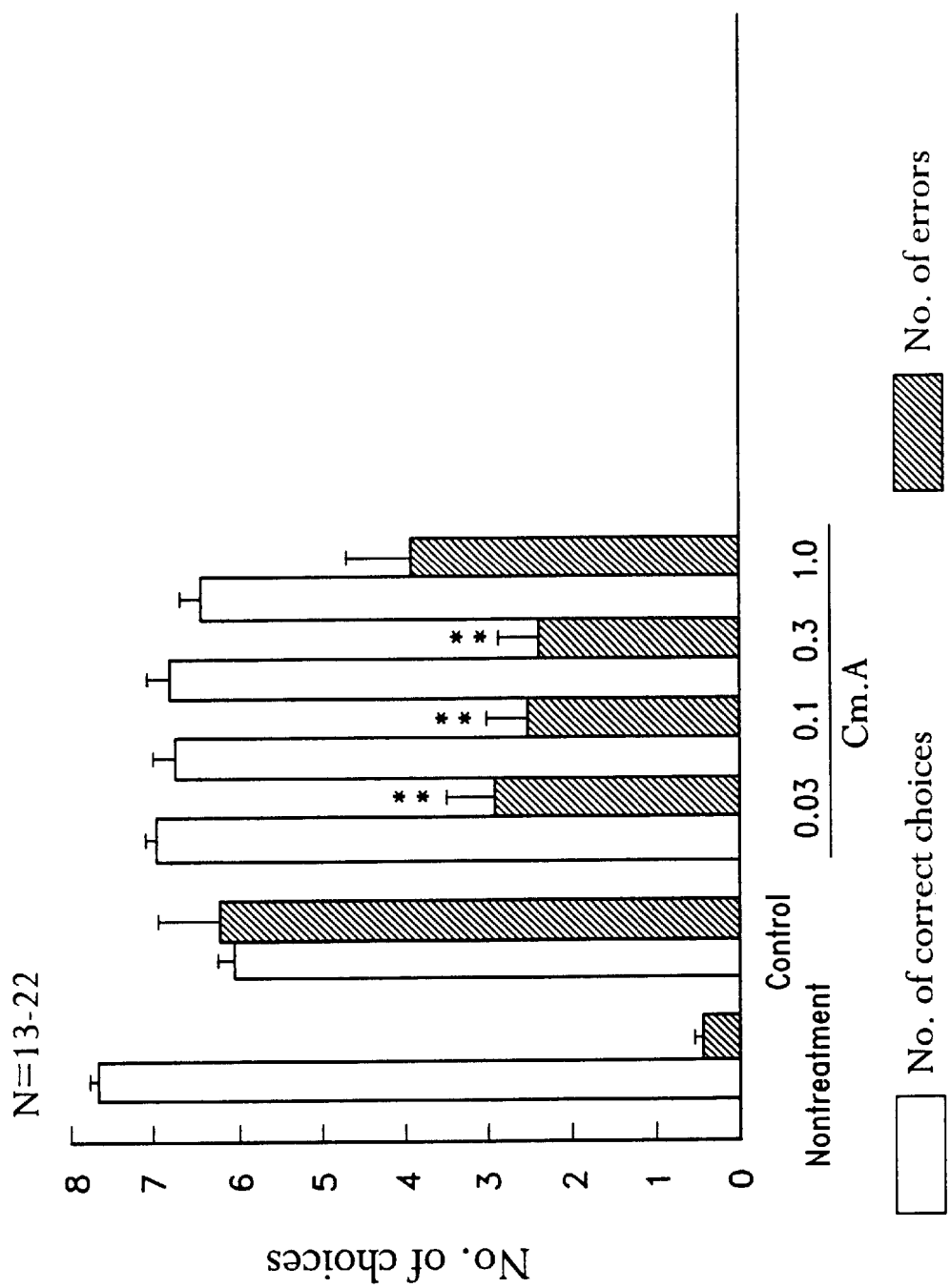
FIG. 9 provides graphic results of the effects of Cm.A on spatial memory deficit induced by scopolamine in a radial maze task. Each column represents the mean with S.E.M. *,**: $P<0.05$, $0.01$ vs. control.

Treatment with i.p. scopolamine (0.5 mg/kg) significantly caused a decrease in the correct choices and an increase in errors in spatial memory-established rats. A oral dose of Cm.A (0.03~0.3 mg/kg) significantly improved the deficit of spatial cognition. See FIG. 9.

2. Medial Septal Nucleus (SEP) Lesion-Induced Deficit in Spatial Memory

SEP (Bregma, A: 0.2 mm, L: −1.0 mm, H: −5.8 mm) was lesioned by microinjection with ibotenic acid (10 $\mu$g) similarly to that of the BF lesion of Example 4A(3).

Figure 10:
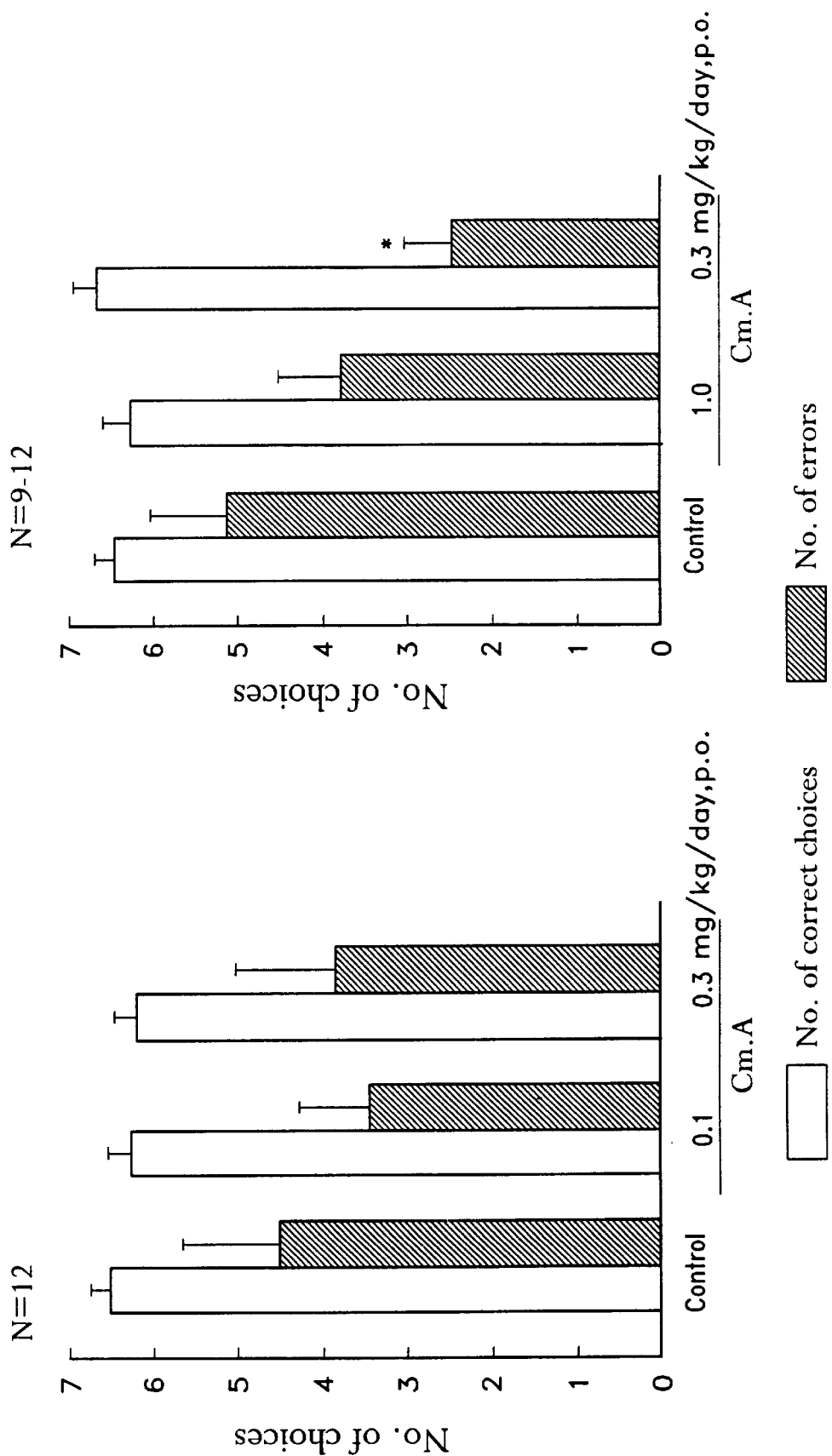
FIG. 10 provides graphic results of the effects of repeated treatment for 2 weeks with Cm.A on spatial memory deficit induced by SEP lesion in a radial maze task. Each column represents the mean with S.E.M. *: $P<0.05$ vs. control.

After repeated treatment for 2 weeks, Cm.A (3.0 mg/kg/day) significantly improved the deficit of spatial memory. See FIG. 10.

C. Water Maze

Using young (2 month-old) male Wistar rats or young (2 month-old) and old (22 month-old) male Fischer 344 rats, the anti-amnestic effect of the compounds in a Morris water maze task (Morris, R. *J. Neurosci. Meth.* 27 (1984)) was observed under the following parameters. For each training trial, the rat was placed in the water (22° C.) such that the animal faced the wall of a circular pool (150 cm in diameter, 45 cm in height), and started at one of five starting points (selected randomly). In each trial, the latency period to escape onto the hidden platform (fixed in the middle of one quadrant, 2 cm below the surface of water) was recorded. These procedures were repeated once or twice a day during the experimental period.

1. Scopolamine-Induced Deficit in Spatial Learning

Figure 11A:
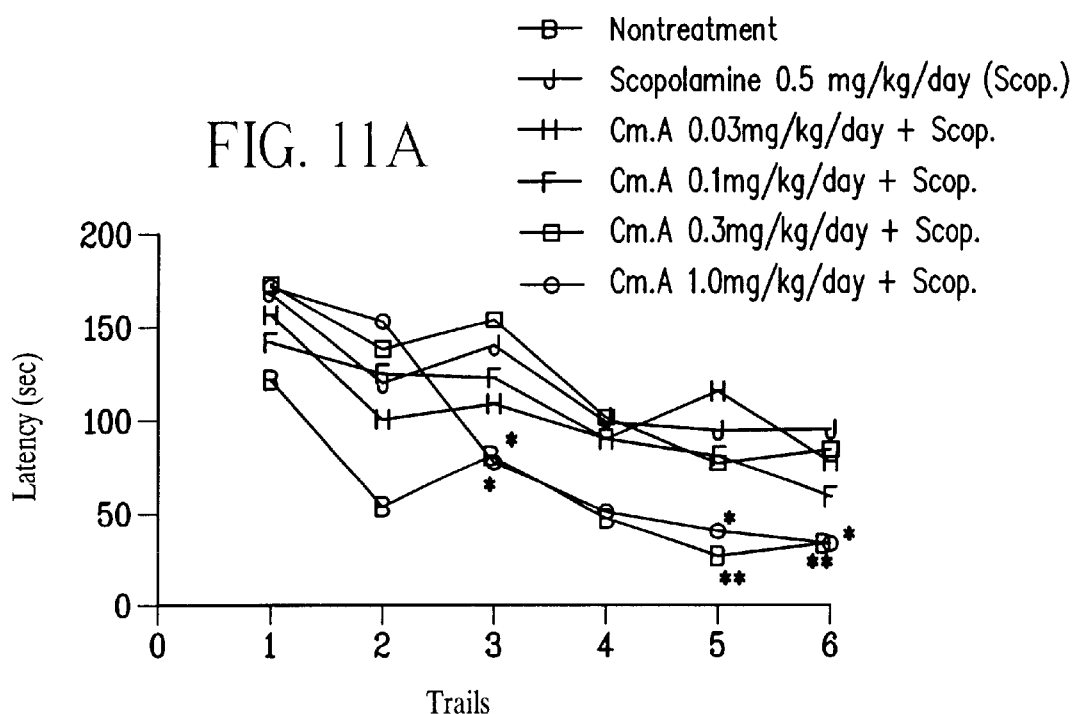
FIGS. 11A–B provide graphic results of the effects of Cm.A (11A) and THA (11B) on scopolamine-induced spatial memory deficit in a water maze task. Each point represents the mean values of 10 to 12 rats. *,**: $P<0.05$, $0.01$ vs. scopolamine.
Figure 11B:
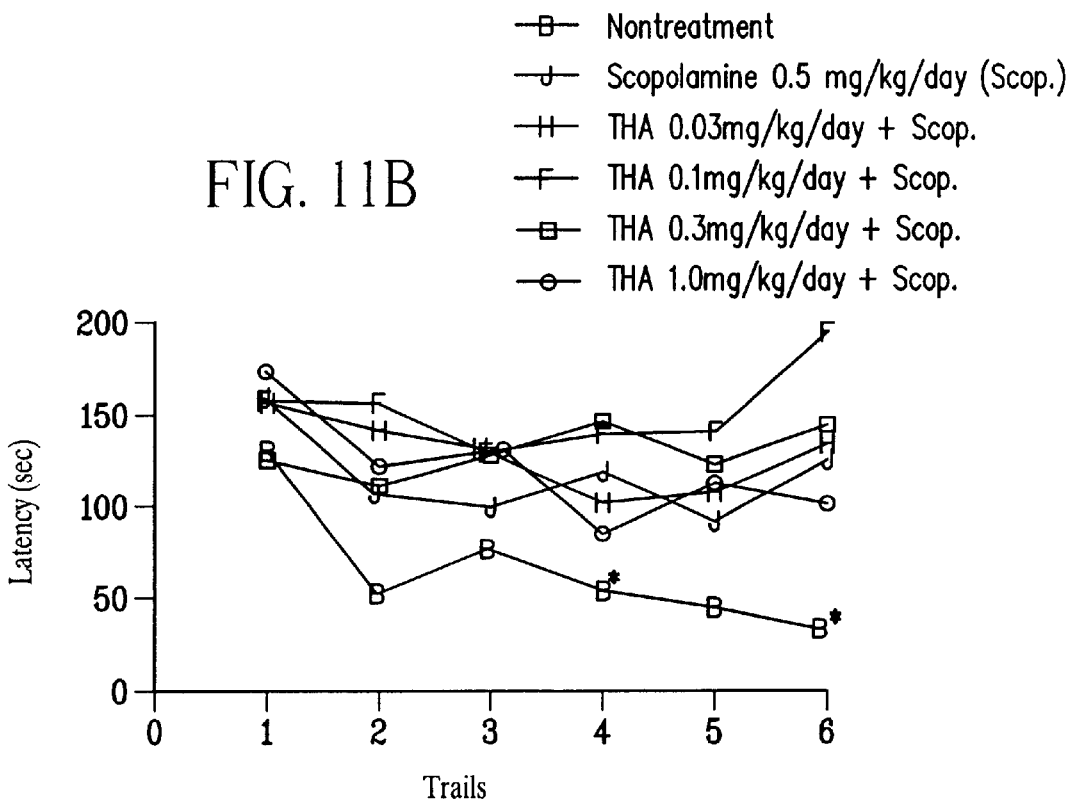

A total of 6 trials (2 trials on $1^{st}$ day, and 1 trial after $2^{nd}$ day) were conducted to observe the effects of the test compounds. Scopolamine (0.5 mg/kg, i.p.) and the test compounds (p.o.) were administered 30 and 60 minutes before each trial, respectively. Results are summarized in FIG. 11.

The latency period to escape onto the platform declined gradually as the number of trials increased in the nontreated controls. Scopolamine significantly inhibited this learning processes. Cm.A (1.0 mg/kg/day) improved the deficit in spatial learning induced by scopolamine. THA showed no significant effect in this experiment.

2. Basal Forebrain (BF) Lesion-Induced Deficit in Spatial Learning

Figure 12A:
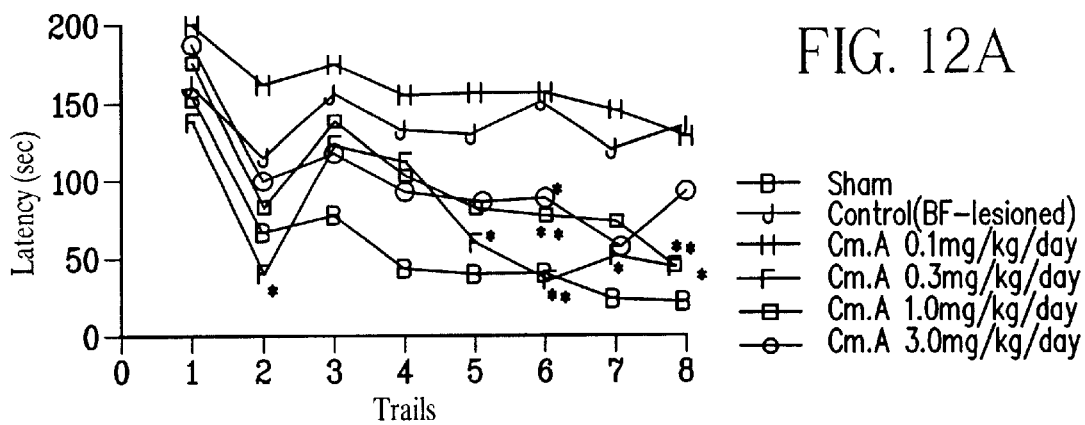
FIGS. 12A–C provide graphic results of the effects of Cm.A (12A), THA (12B) and E2020 (12C) on BF lesion-induced memory deficit in a water maze task. Each point represents the mean values of 7 to 12 rats. *, ** : $P<0.05$, $0.01$ vs. BF-lesioned control.
Figure 12B:
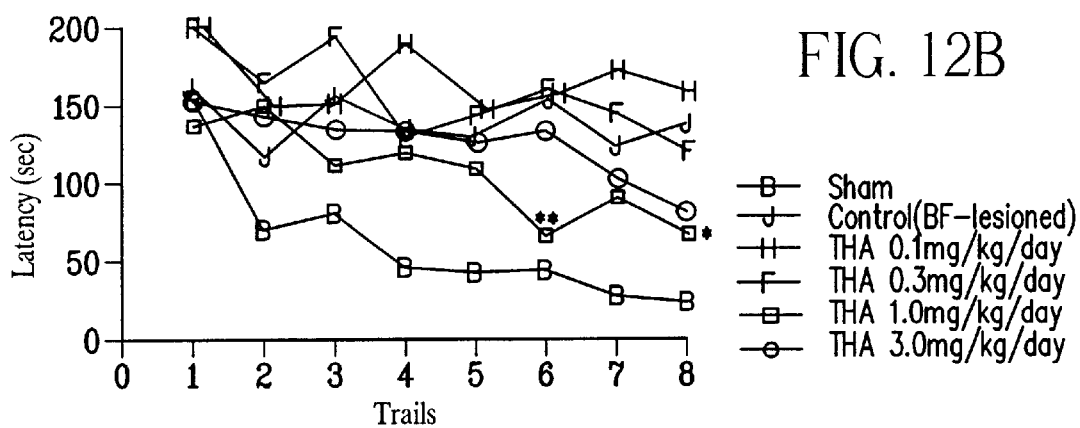
Figure 12C:
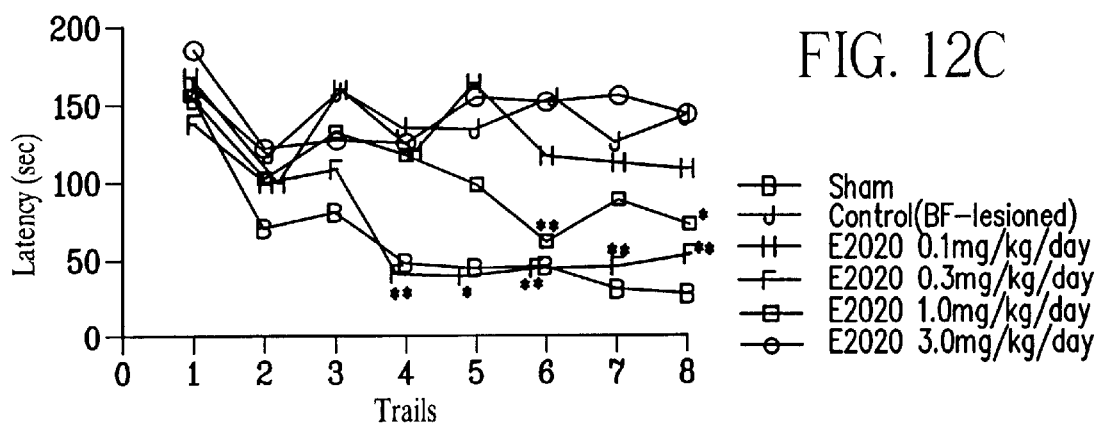

The escape latency period for BF-lesioned rats did not decline even after repeated learning for 7 days. Oral treatment with 0.3, 1.0 and 3.0 mg/kg/day of Cm.A improved the deficit of spatial learning. THA (1.0 mg/kg/day) and E2020 (0.3 and 1.0 mg/kg/day) also improved this type of deficit induced by the BF-lesion. See FIG. 12.

3. Effect on Aged Rats

Figure 13A:
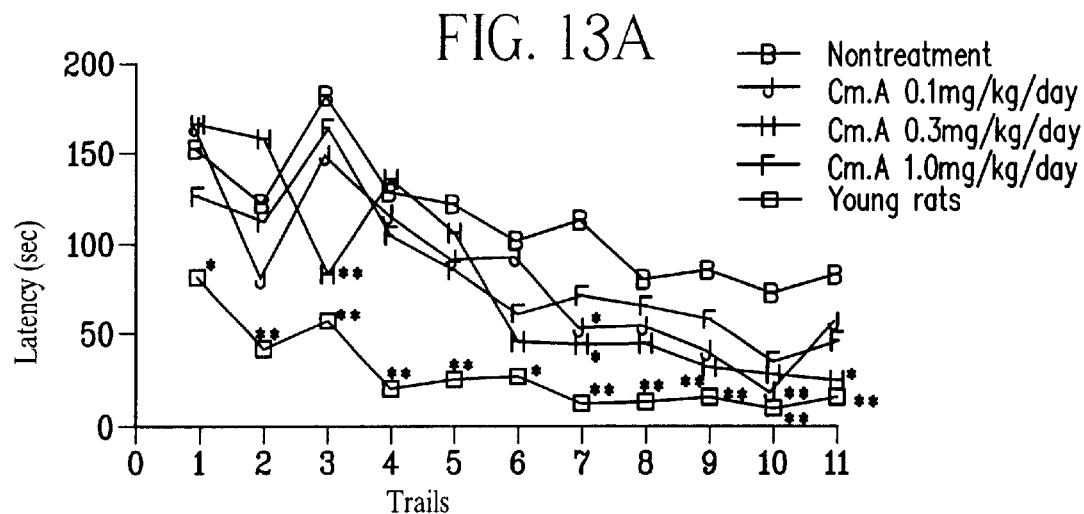
FIGS. 13A–B provide graphic results of improvement of spatial learning by the treatment with Cm.A (13A) and THA (13B) in aged rats. Each point represents the mean values of 7 to 10 rats. *,**: $P<0.05$, $0.01$ vs. nontreatment.
Figure 13B:
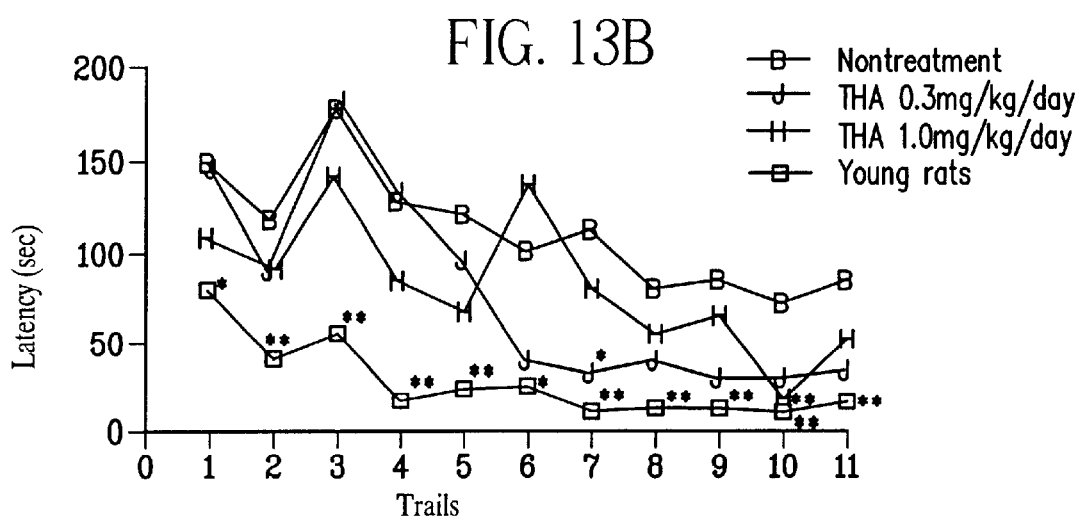
Figure 14A:
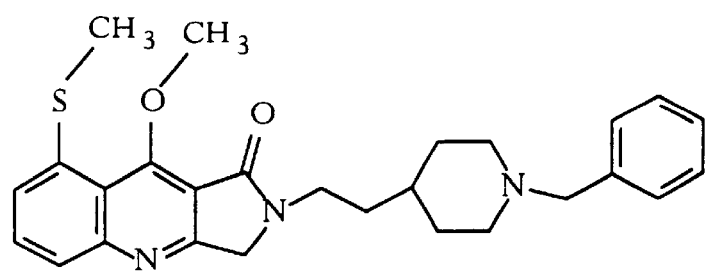
FIGS. 14A–F are the structures for a variety of compounds related to Cm.A depicted as Cm.B through Cm.G, respectively, that are also acetylcholine enhancers.
Figure 14B:
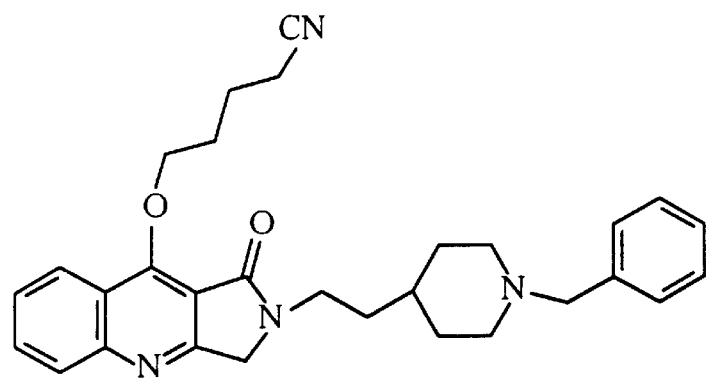
Figure 14C:
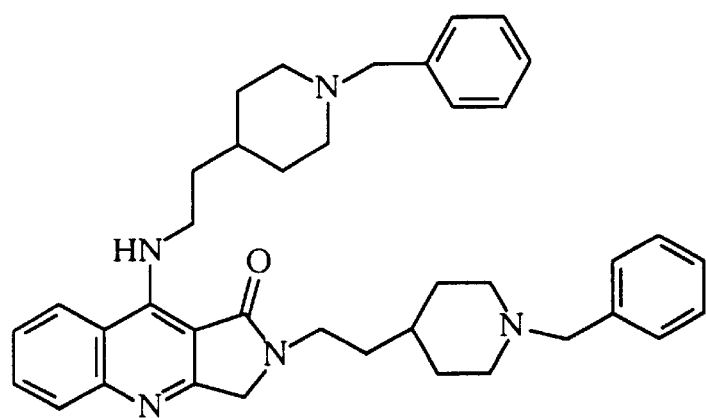
Figure 14D:
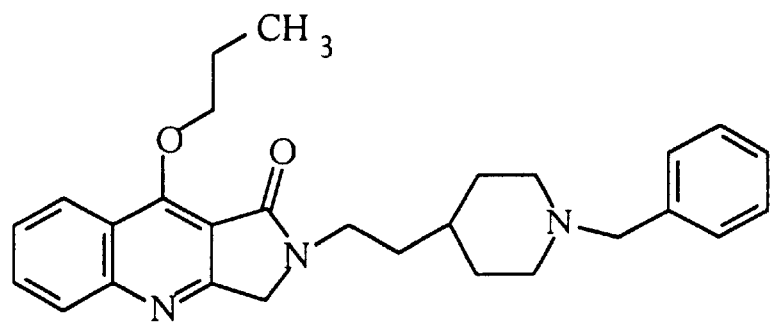
Figure 14E:
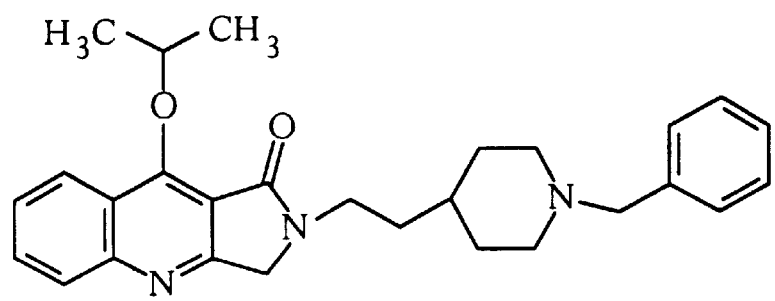
Figure 14F:
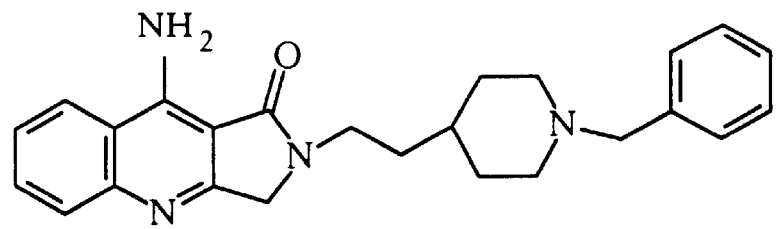

As compared with young rats, aged rats (22 month-old) were unable shorten the escape latency period. Even after the $11^{th}$ trial, only a partial decrease in the latency period was evident in the aged rats. However, Cm.A gradually improved the deficit of spatial learning to a level nearly equivalent to young rats. THA evidenced similar activity in this experiment. See FIG. 13.

Example 6

Human Phase I Clinical Analysis.

A Phase IA clinical trial was conducted as a single-dose, double-blind, placebo-controlled, dose-escalation study.

Figure 1B:
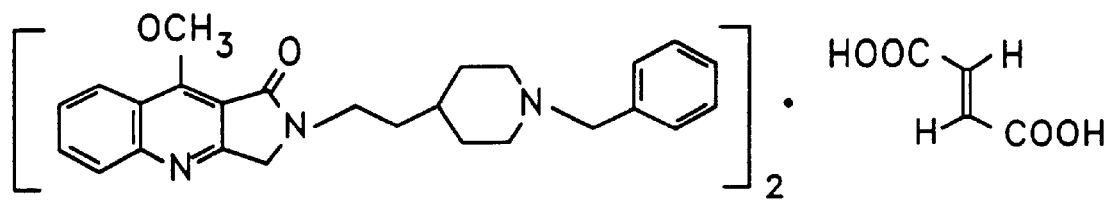
FIG. 1B shows the structure of a particularly preferred salt of the compound of FIG. 1A, 2-[2-(1-benzylpiperizin-4-yl)ethyl]-2,3-dihydro-9-methoxy-1H-pyrrolo[3,4-b]quinolin-1-one hemifumarate ("Cm.A").

This study investigated the safety and pharmacokinetic profile of the particularly preferred salt (depicted in FIG. 1B; N-[2-( 1-benzylpiperizin-4-yl)ethyl]-2,3-dihydro-9-methoxy-1H-pyrrolo[3,4-b]quinolin-1-one hemifumarate) of the compound of FIG. 1A, N-[2-(1-benzylpiperzin-4-yl) ethyl]-2,3-dihydro-9-methoxy-1H-pyrrolo[3,4-b] quinolin-1-one. The compound was administered orally in doses from 2 mg to 180 mg to healthy volunteers (male and female), aged 50–75 years, under fasting conditions. A total of 68 individuals were enrolled in the study and completed the trial. A maximum tolerated dose was not identified in this study, i. e., even at 180 mg, there were insufficient adverse events to establish a true "maximum tolerated dose" in this study. Indeed, there were no clinically significant changes in any of the safety parameters monitored in the study (vital signs, ECG, blood chemistry, hematology, urinalysis, and physical examination). There were no serious adverse events reported; seven mild adverse events occurred during the study in individuals receiving the compound, and those that may have possibly been related to the compound included headache and nausea.

It is noted that the recommended dose for the approved AChE inhibitor E2020 (ARICEPTÒ) is 5 or 10 mg per day. See, *Physicians Desk Reference,* 53$^{rd}$ Edition, 1999, pages 960–963. Although a clinically-established inhibitor of AChE, E2020 is not described as having any effect upon the 5HT3 receptor.

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. An acetyicholine enhancer selected from the group consisting of the chemical compounds represented by the following structure:

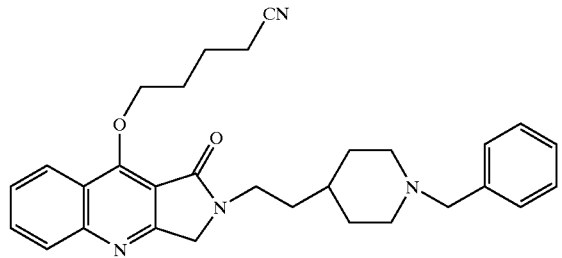

and pharmaceutically acceptable salts thereof.

* * * * *

UNITED STATES PATENT AND TRADEMARK OFFICE
CERTIFICATE OF CORRECTION

PATENT NO.     : 6,586,596 B2
DATED          : July 1, 2003
INVENTOR(S)    : Susumo Sato and Tadayuki Koda It is certified that error appears in the above-identified patent and that said Letters Patent is hereby corrected as shown below:

<u>Title page</u>,
Item [75], Inventors, please delete "Derek T. Chalmers"

<u>Column 1</u>,
Lines 16-18, please delete "60/136,887 entitled "Acetylcholine Enhancers" filed June 1, 1999 in the names of Derek T. Chalmers, Susumo Sato and Tadayuki Koda" and insert therefor -- 60/136,887, filed via Express Mail on June 1, 1999. --

Signed and Sealed this

Sixteenth Day of March, 2004

JON W. DUDAS
*Acting Director of the United States Patent and Trademark Office*